US008109917B2

(12) United States Patent
Yeakley et al.

(10) Patent No.: US 8,109,917 B2

(45) Date of Patent: Feb. 7, 2012

(54) TWISTABLE MEDICATION DISPENSING SYSTEM

(75) Inventors: Rourke M. Yeakley, Eagle, ID (US); Charles Leslie Floyd, Jr., Emeryville, CA (US)

(73) Assignee: Rourke M. Yeakley, Eagle, ID (US)

( * ) Notice: Subject to any disclaimer, the term of this patent is extended or adjusted under 35 U.S.C. 154(b) by 244 days.

(21) Appl. No.: 12/689,165

(22) Filed: Jan. 18, 2010

(65) Prior Publication Data

US 2011/0178494 A1 Jul. 21, 2011

(51) Int. Cl.
*A61B 19/00* (2006.01)

(52) U.S. Cl. ........ 604/410; 604/403; 604/414; 604/415; 604/416

(58) Field of Classification Search .................... 433/90; 604/205, 236, 410, 414, 416; 128/218; 222/80, 222/129; 206/363–366; 220/225.01, 500–501
See application file for complete search history.

(56) References Cited

U.S. PATENT DOCUMENTS 2,634,856 A 4/1953 Perkins
2,673,563 A 3/1954 Kwast
2,754,590 A 7/1956 Cohen
2,787,269 A 4/1957 Cohen
3,302,644 A 2/1967 Kennedy et al.
3,327,710 A 6/1967 Freeberg et al.
4,027,985 A 6/1977 Loesser
4,059,109 A 11/1977 Tischlinger
4,410,323 A 10/1983 Hodosh et al.
4,457,427 A 7/1984 Cafiero
4,548,601 A 10/1985 Lary
4,632,244 A 12/1986 Landau
4,954,239 A 9/1990 Mueller
5,037,389 A 8/1991 Dooley
5,058,770 A * 10/1991 Herold et al. .................. 222/80
5,137,511 A * 8/1992 Reynolds ........................ 604/88
5,196,001 A 3/1993 Kao
5,199,567 A 4/1993 Discko, Jr.
5,286,257 A 2/1994 Fischer (Continued)

FOREIGN PATENT DOCUMENTS

CA 2 526 115 3/2005

(Continued)

OTHER PUBLICATIONS

Action Regarding Application No. CA 2,526,115, Dec. 7, 2010, Canadian Intellectual Property Office, Canada.

(Continued)

*Primary Examiner* — Leslie Deak
*Assistant Examiner* — Xin Xie
(74) *Attorney, Agent, or Firm* — Frank J. Dykas; Dykas & Shaver, LLP

(57) ABSTRACT

Disclosed is a dispenser having a first chamber containing a first fluid and a second chamber containing a second material. Each chamber has screw threads that are selectively joinable so that the first and second chambers are twistable relative to one another. The first chamber includes an open top end that is, before use, covered with a breakable membrane. A breaker ring is located within the second chamber and is configured to break the breakable membrane when the dispenser is transitioned between an extended position and a compact position. In the compact position with the breakable membrane broken, the first fluid and second material form a mixture that can be dispensed via an opening in an openable tip.

16 Claims, 25 Drawing Sheets

U.S. PATENT DOCUMENTS

| | | | | |
|---|---|---|---|---|
| 5,298,248 | A | 3/1994 | Hugues et al. | |
| 5,593,697 | A | 1/1997 | Barr et al. | |
| 5,609,581 | A | 3/1997 | Fletcher et al. | |
| 5,761,885 | A | 6/1998 | Hansen | |
| 5,819,921 | A | 10/1998 | Schmid | |
| 6,200,295 | B1 | 3/2001 | Burchett et al. | |
| 6,244,433 | B1 * | 6/2001 | Vieu | 206/221 |
| 6,349,850 | B1 | 2/2002 | Cheikh | |
| 6,386,872 | B1 | 5/2002 | Mukasa et al. | |
| 6,779,566 | B2 | 8/2004 | Engel | |
| 6,869,284 | B2 | 3/2005 | Aoyagi et al. | |
| D536,991 | S | 2/2007 | Dlugolecki | |
| 7,452,350 | B2 | 11/2008 | Yeakley | |
| D598,538 | S | 8/2009 | Yeakley | |
| 2002/0108875 | A1 | 8/2002 | Feinberg et al. | |
| 2003/0085148 | A1 | 5/2003 | Boehm, Jr. et al. | |
| 2005/0010190 | A1 | 1/2005 | Yeakley | |
| 2005/0040065 | A1 | 2/2005 | O'Heeron | |
| 2005/0211595 | A1 | 9/2005 | Hull | |
| 2007/0089905 | A1 | 4/2007 | Lee | |
| 2008/0108936 | A1 | 5/2008 | Timm | |
| 2008/0108951 | A1 | 5/2008 | Jerde et al. | |
| 2008/0116106 | A1 | 5/2008 | Lampropoulos et al. | |
| 2008/0121553 | A1 | 5/2008 | Gobel | |
| 2008/0125721 | A1 | 5/2008 | Timm | |
| 2008/0179345 | A1 * | 7/2008 | Patey et al. | 222/129 |

FOREIGN PATENT DOCUMENTS

| | | |
|---|---|---|
| DE | 24 57 994 | 6/1976 |
| EP | 1 163 918 | 12/2001 |
| EP | 1 308 149 | 5/2003 |
| WO | WO 98/15314 | 4/1998 |
| WO | WO 2005/009327 | 2/2005 |

OTHER PUBLICATIONS

International Preliminary Report on Patentability, Jan. 9, 2006, The International Bureau of WIPO.

* cited by examiner

TWISTABLE MEDICATION DISPENSING SYSTEM

FIELD OF THE INVENTION

The invention generally relates to medication dispensing systems and more particularly to a portable, pre-measured medication dispensing systems.

BACKGROUND OF THE INVENTION

One of the greatest benefits of modern medicine has been the ability of antibiotics and other medications to cure and treat diseases that have plagued mankind from the beginning of time. While many individuals have access to medications whose usage can be lifesaving, the availability and dispersal of these medications to individuals that truly need them throughout the world has not yet been properly established. One of the reasons for which the dispersal of medication has not been effective in all locations is that, in many locations, individuals do not know how much medication to impart to reach the desired dosing requirements for efficacy while also preventing damage to the individual. Another problem that occurs is that, in some instances, the ability to take the medication cannot be effectively performed because of a lack of dispensatory materials at the designated location.

Additionally, medication to be dispensed in small amounts is often sold in large containers and sent in shipments that may require refrigeration. Thus, the cost of a relatively small amount of medication is increased by the cost of transporting the medication to the desired location and storing the medication. In other instances, the individual needing to use medication is required to purchase a greater amount of medication than is actually needed. In these circumstances the cost of the more-than-needed medication can be prohibitive for the individual.

Further, the administration of medication often requires more time, knowledge, or precision than an individual is able to apply to the administration of medication. When this occurs, an individual could measure and utilize the medication inappropriately. As a result, individuals may become ill from taking too much of the medication or find that the medication is ineffective against the disease to be treated when improperly-small dosages of the medications are administered. This in turn can lead to a variety of otherwise-avoidable health issues including sickness, discomfort, pain, irritability, and even death to individuals who fail to take the proper medication at the proper times or in the proper amounts.

As a particular example, in treating bacterial inventions and other bio-hazards, including the defenses against organisms used as bio-weaponry, the improper use or dosing of antibiotics can lead to mutations of the bacteria involved, leading to the creation of medication-resistant bacteria that will not respond to the traditionally-outlined antibacterial regimens.

SUMMARY OF THE INVENTION

The present dispenser is a dispensing system for dispensing pre-measured doses of selected materials, particularly medications, in a safe and effective manner and in any of a variety of circumstances. The dispenser can be utilized by individuals with little to no medical training and without the need to measure medications to be dispensed.

The dispenser includes a first chamber containing a first fluid, such as a reconstituting liquid, and a second chamber containing a second material, such as a medication powder. The first chamber has first screw threads lining an external area. The first chamber further has an open top end that is covered by a breakable membrane. The second chamber has second screw threads lining an internal area. The second chamber further has an openable tip, which, when opened defines an opening. Contained within the second chamber is a breaker ring, the lower edge of which is configured to break the breakable membrane when the lower edge of the breaker ring is brought into forced contact with the breakable membrane.

The first and second screw threads are configured to interact with one another such that the first and second chambers can be joined via the screw threads. The first chamber and second chamber are twistable, relative to one another, to move the chambers closer to or further away from one another. The first chamber and second chamber are to be twisted into an extended position in which the lower edge of the breaker ring is situated so as to be above the breakable membrane. The first chamber and second chamber can then be twisted relative to each other to bring the lower edge of the breaker ring into forced contact with the breakable membrane, eventually resulting in breakage of the breakable membrane. Additional twisting of the first chamber and second chamber relative to one another transitions the dispenser to a compact position. In the compact position the first fluid within the first chamber and the second material within the second chamber are able to join into a mixture. When the openable tip is opened, the mixture can be forced out of the dispenser to be administered to a patient.

Alternatively, as the first and second screw threads interact to allow twisting of the first and second chambers both closer to and further away from one another, the two chambers of the dispenser can be unconnected from one another and the material within the second chamber, which could be medication in a powder form, dispensed by emptying the second chamber via the open bottom end of the chamber, without having to open the openable tip. Similarly, the material within the first chamber can be separately dispensed, when the two chambers of the dispenser are unconnected, by breaking the breakable membrane and emptying the contents of the first chamber via the open top end of the first chamber.

The dispenser is further configured to be stored and transported within a storage container. The storage container is formed, at least in part, by a container wall. In some embodiments, a puncturing device protrudes from the container wall and is configured to enable puncturing of a puncturable openable tip in the second chamber by applying the openable tip against the puncturing device with some pressure. Accordingly, the user of the dispensing system need not have available a separate puncturing device.

In any regard, this dispenser allows a pre-measured dosage of medication to be administered without having to use separate medication delivery devices and without the necessity of separately or carefully measuring the material to be dispensed. Having the material to be dispensed contained within one device lessens the risk of spillage and waste of the material. Further, the dispenser is used with only easy manipulation of a simple and safe device as no external sharp objects need be utilized. Thus, the dispenser can be utilized in a broad variety of circumstances by individuals with little or no training, either in medicine or in use of the dispenser.

The purpose of the foregoing summary is to enable the public, and especially the scientists, engineers, and practitioners in the art who are not familiar with patent or legal terms or phraseology to determine quickly, from a cursory inspection, the nature and essence of the technical disclosure of the application. The summary is neither intended to define the invention of the application, which is measured by the claims, nor is it intended to be limiting as to the scope of the invention in any way.

Still other features and advantages of the claimed dispensing system will become readily apparent to those skilled in the art from the following detailed description describing preferred embodiments of the dispensing system, simply by way of illustration of the best mode contemplated by carrying out the dispensing system. As will be realized, the dispensing system is capable of modification in various obvious respects all without departing from the invention. Accordingly, the drawings and description of the preferred embodiments are to be regarded as illustrative, and not restrictive.

DESCRIPTION OF THE PREFERRED EMBODIMENTS

Figure 1:
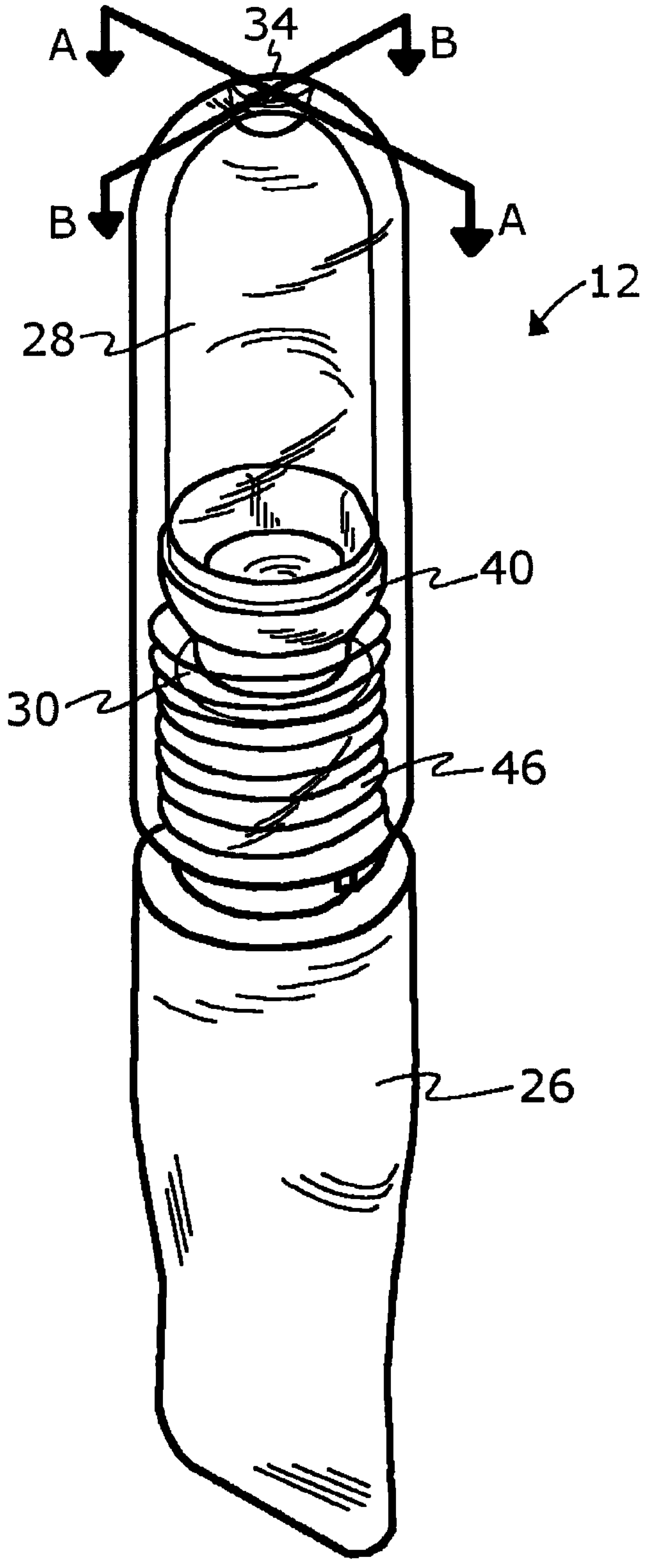
FIG. 1 is an isometric view of the front, top, and right sides of a medication dispenser according to a first embodiment of a dispensing system where the dispenser is in an extended position.
Figure 2:
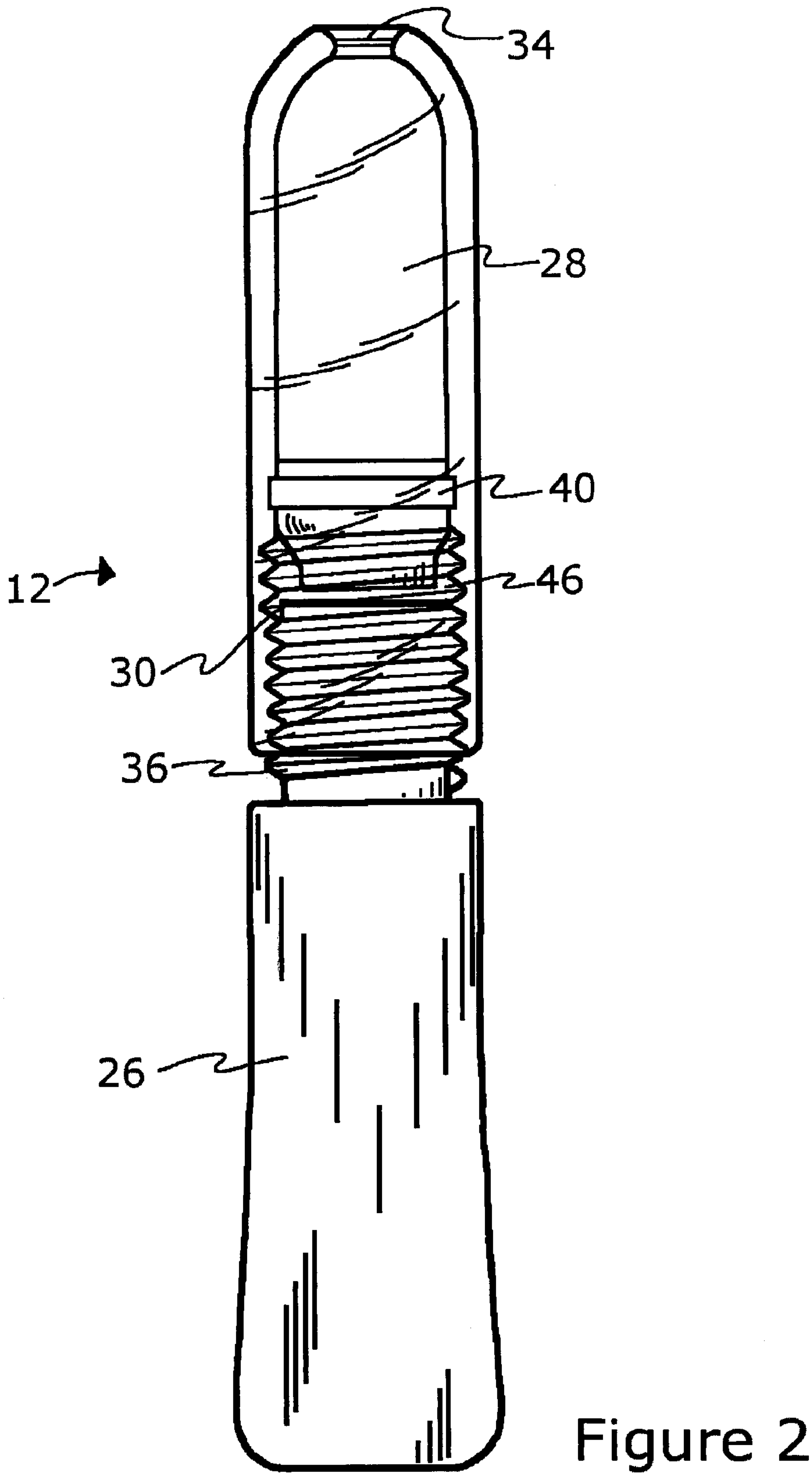
FIG. 2 is an elevation view of the front side of a medication dispenser according to the first embodiment of a dispensing system where the dispenser is in an extended position.
Figure 3:
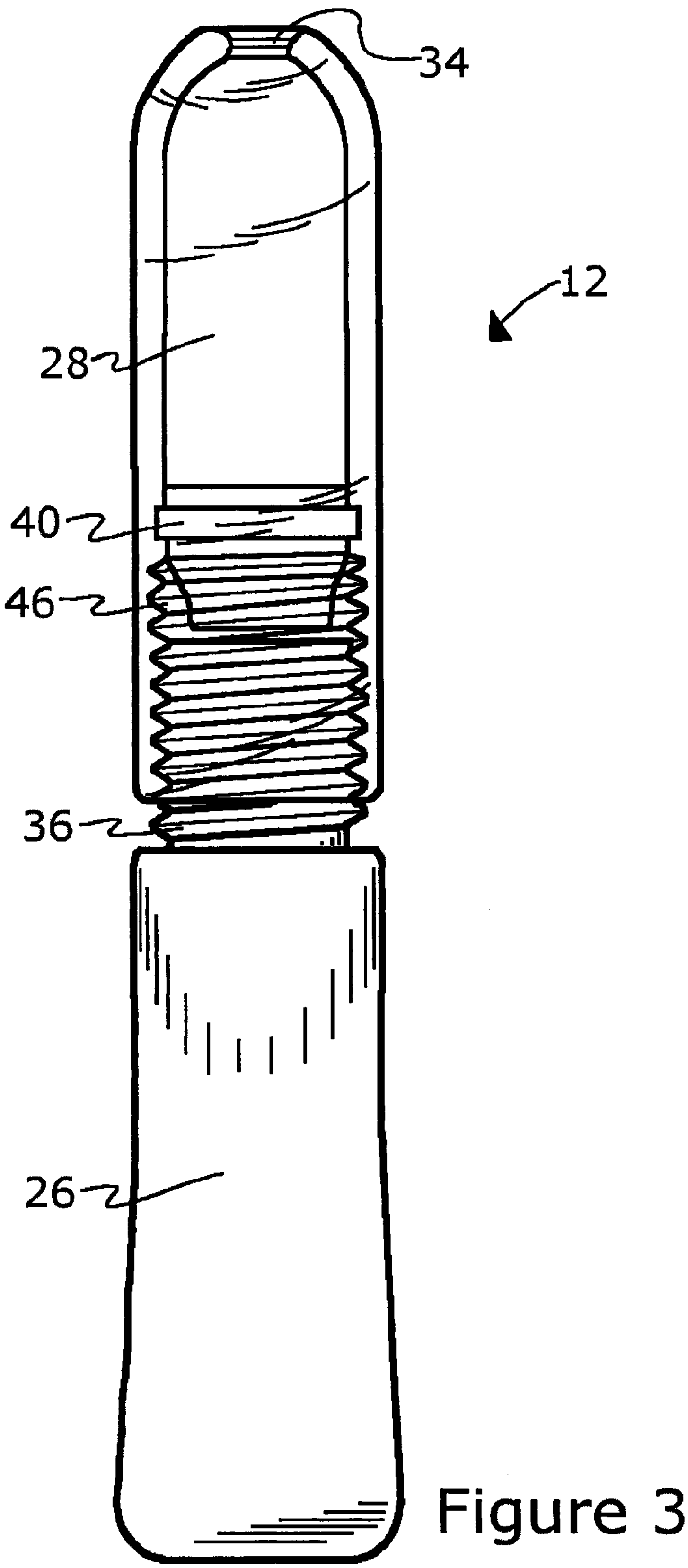
FIG. 3 is an elevation view of the back side of a medication dispenser according to the first embodiment of a dispensing system where the dispenser is in an extended position.
Figure 4:
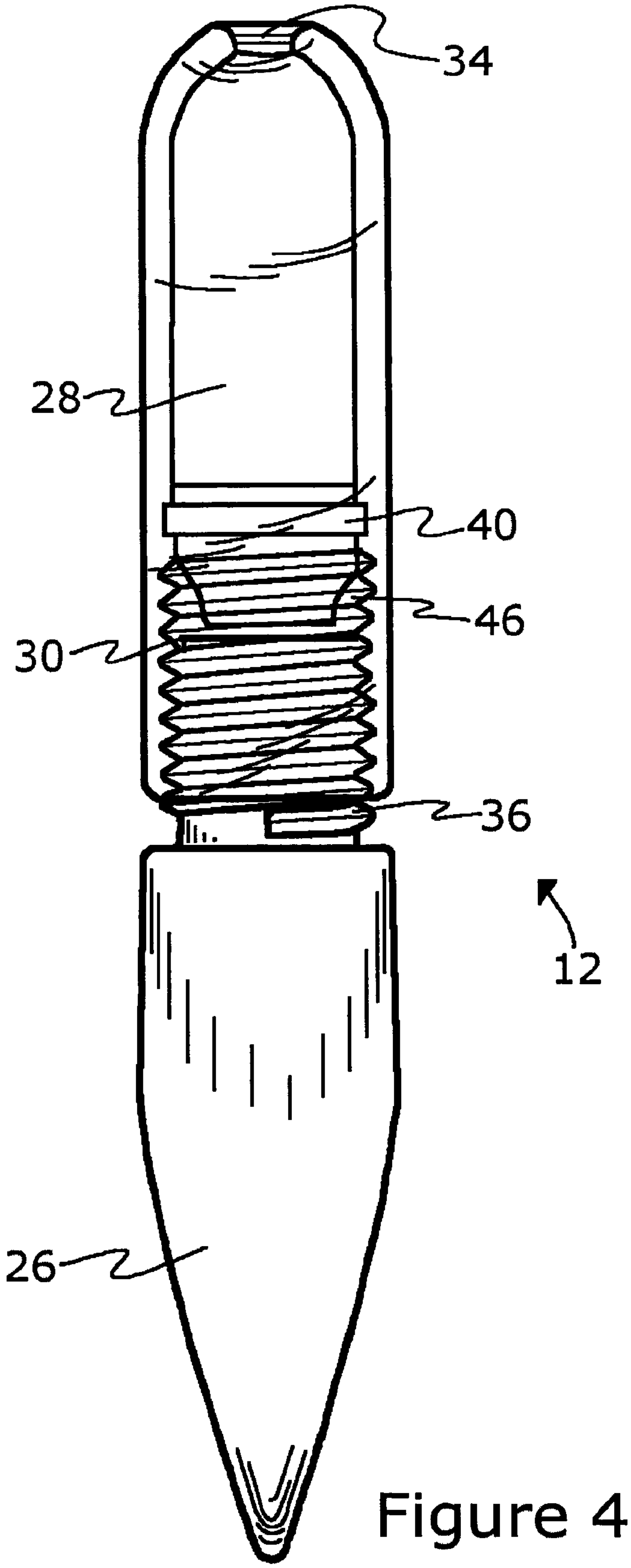
FIG. 4 is an elevation view of the right side of a medication dispenser according to the first embodiment of a dispensing system where the dispenser is in an extended position.
Figure 5:
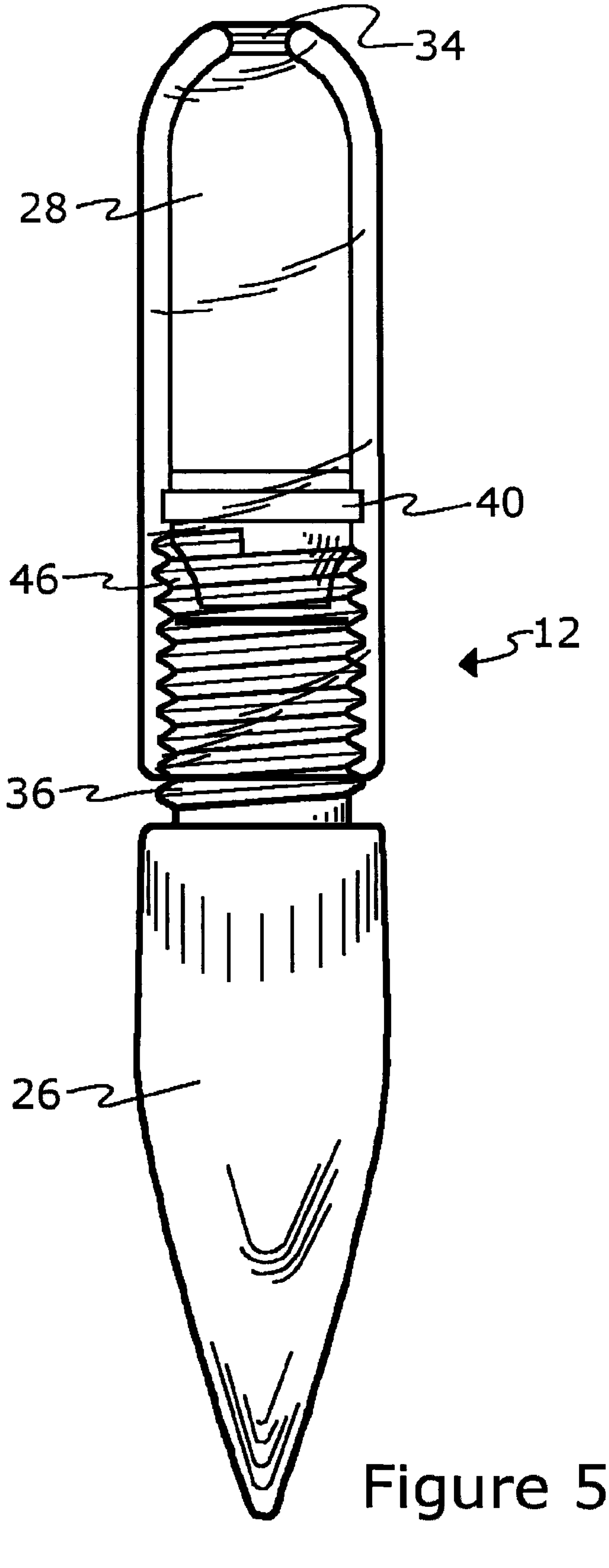
FIG. 5 is an elevation view of the left side of a medication dispenser according to the first embodiment of a dispensing system where the dispenser is in an extended position.
Figure 6:
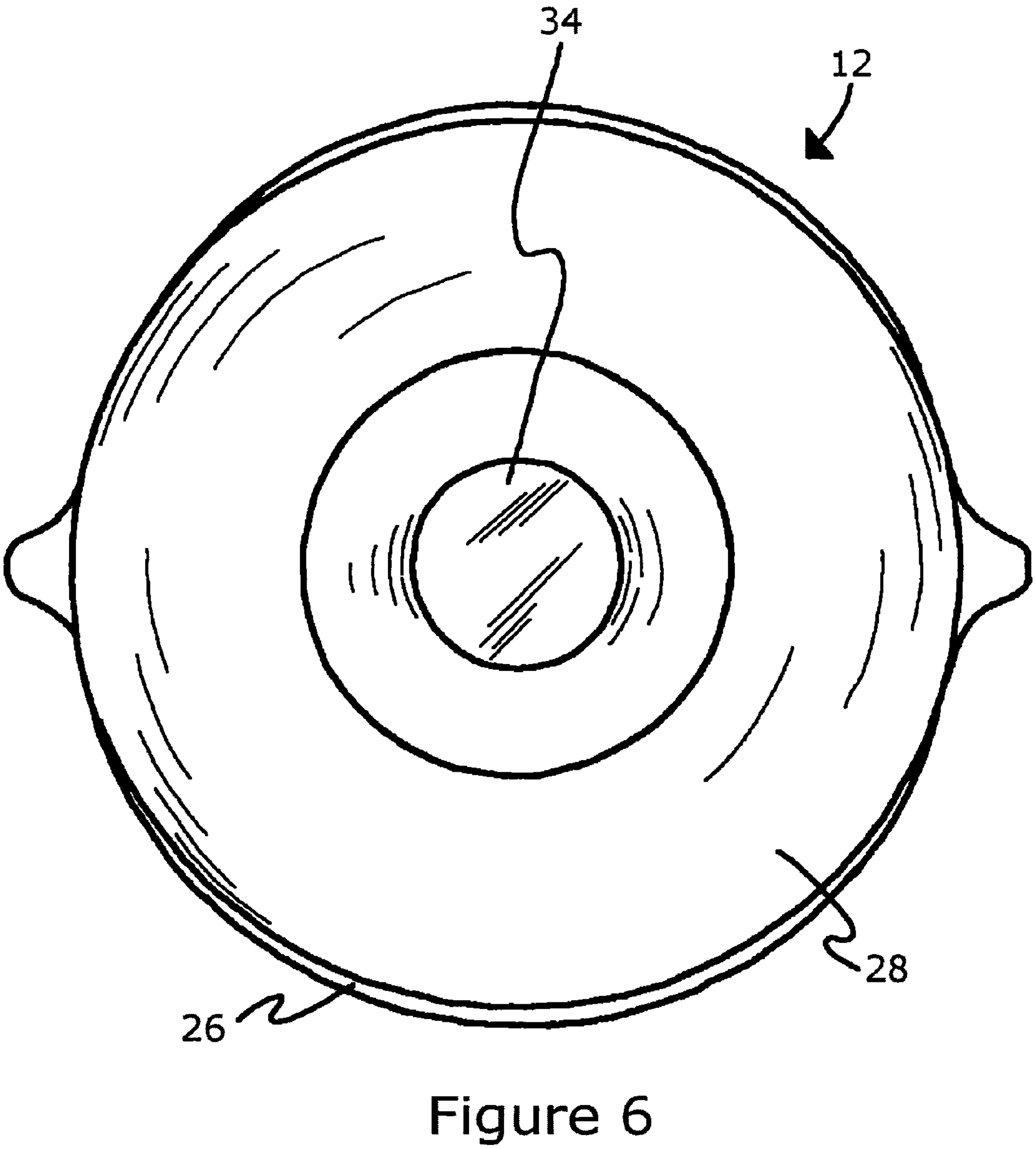
FIG. 6 is a plan view of the top side of a medication dispenser according to the first embodiment of a dispensing system.
Figure 7:
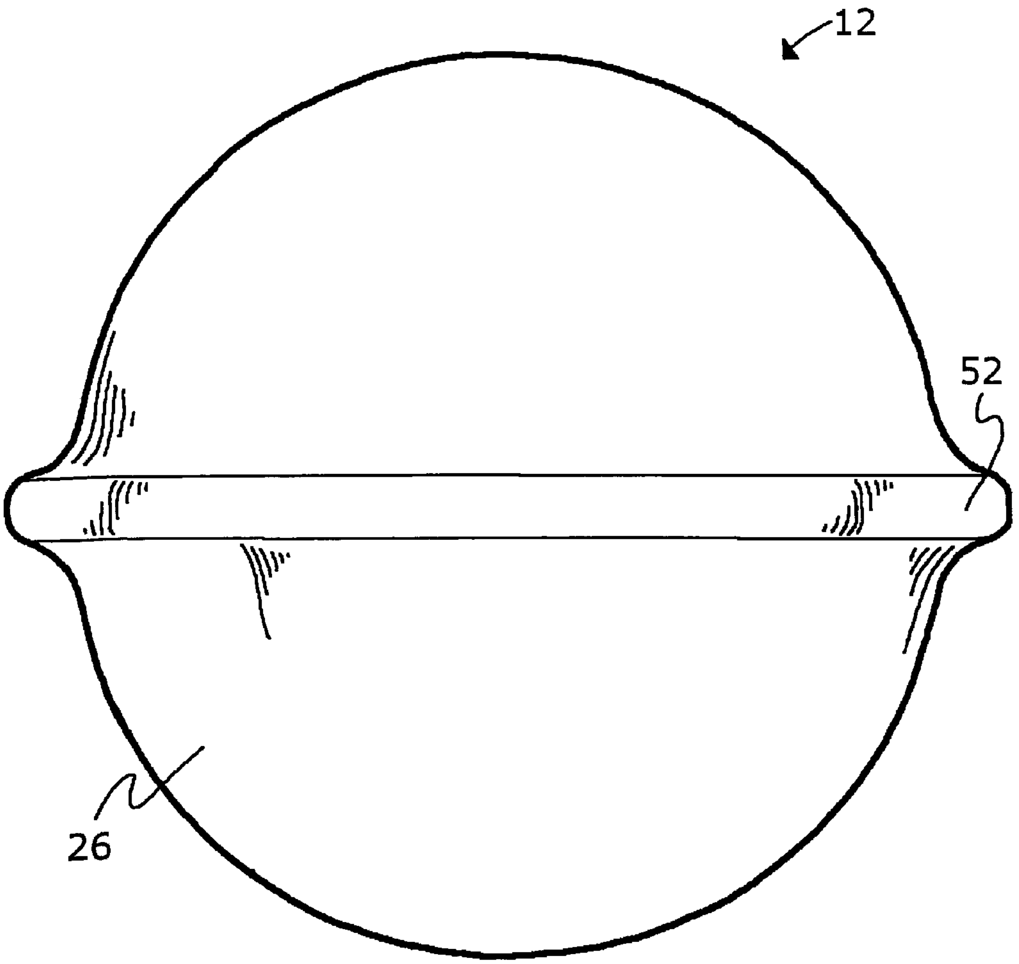
FIG. 7 is a plan view of the bottom side of a medication dispenser according to the first embodiment of a dispensing system.
Figure 8:
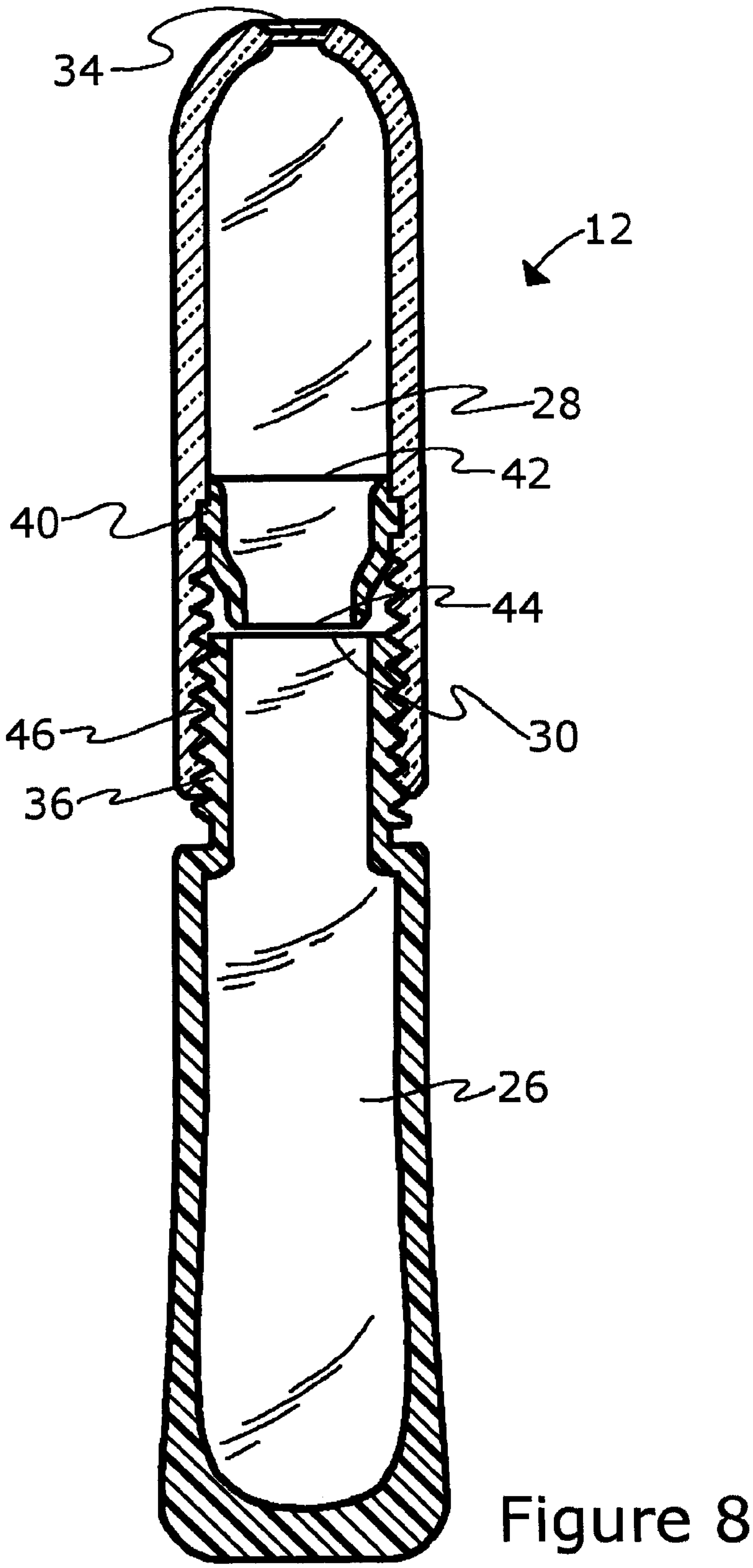
FIG. 8 is a cross-sectional, elevation view, taken along line A-A from the front side, of a medication dispenser according to the first embodiment of a dispensing system where the dispenser is in an extended position.

While the dispensing system is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the medication dispenser as defined in the claims.

As depicted in the drawings, embodiments of the dispensing system provide a system for storing, transporting, and eventually dispensing a pre-measured amount of a mixture of material, such as a medication mixture, where such mixture is originally stored in two separated containers. As such, medication in a solid, powder form can be kept separate from a reconstituting fluid, but in containers quickly and easily combined to provide for mixture of the substances before dispensing of the same without having to use separate dispensing devices and without having to have medical or technological training.

In the following description and in the figures, like elements are identified with like reference numerals. The use of "e.g.," "etc.," and "or" indicates non-exclusive alternatives without limitation unless otherwise noted. The use of "including" means "including, but not limited to," unless otherwise noted.

Figure 10:
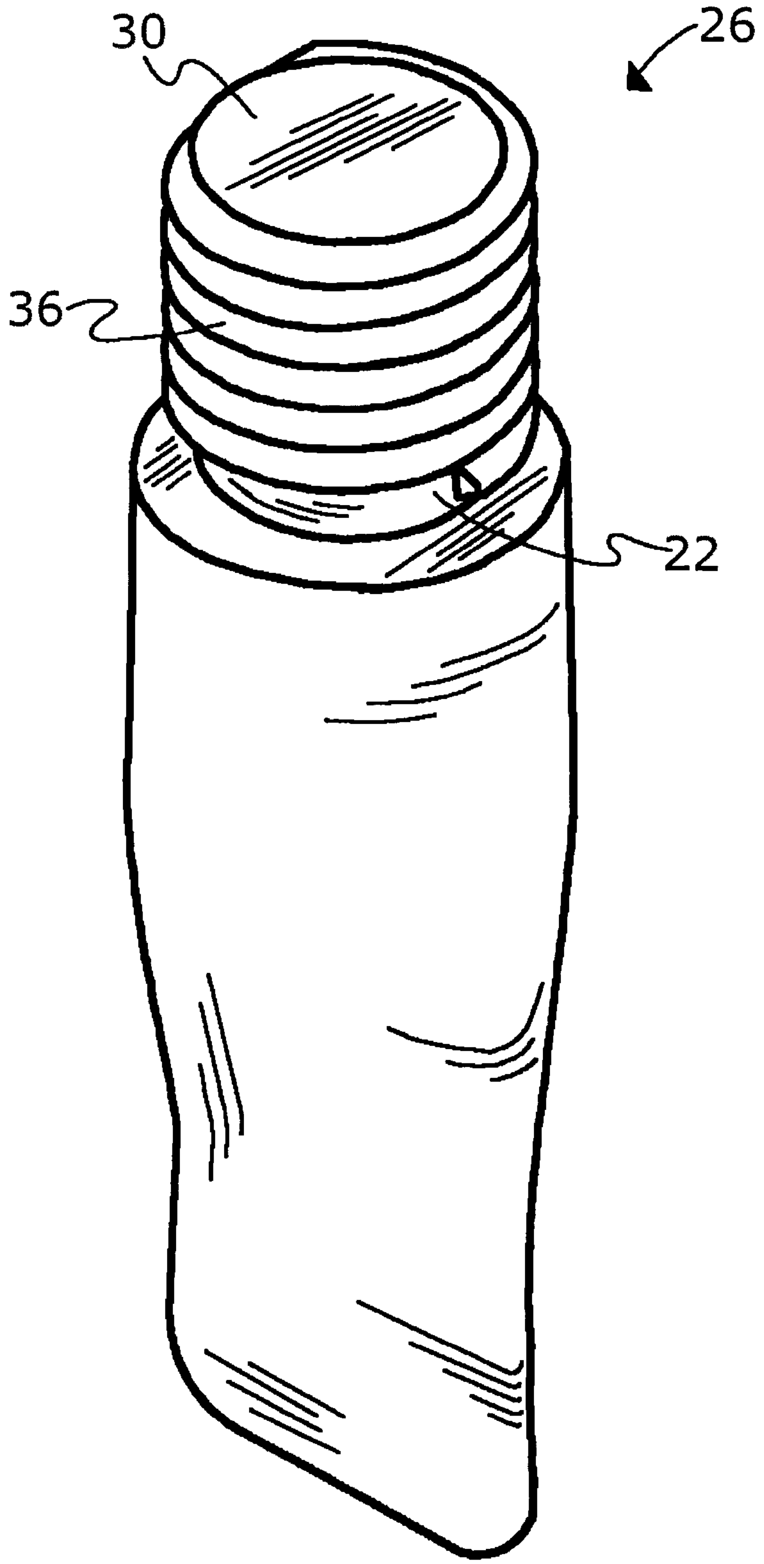
FIG. 10 is an isometric view of the front, top, and right sides of a first chamber of a medication dispenser according to the first embodiment of a dispensing system.
Figure 11:
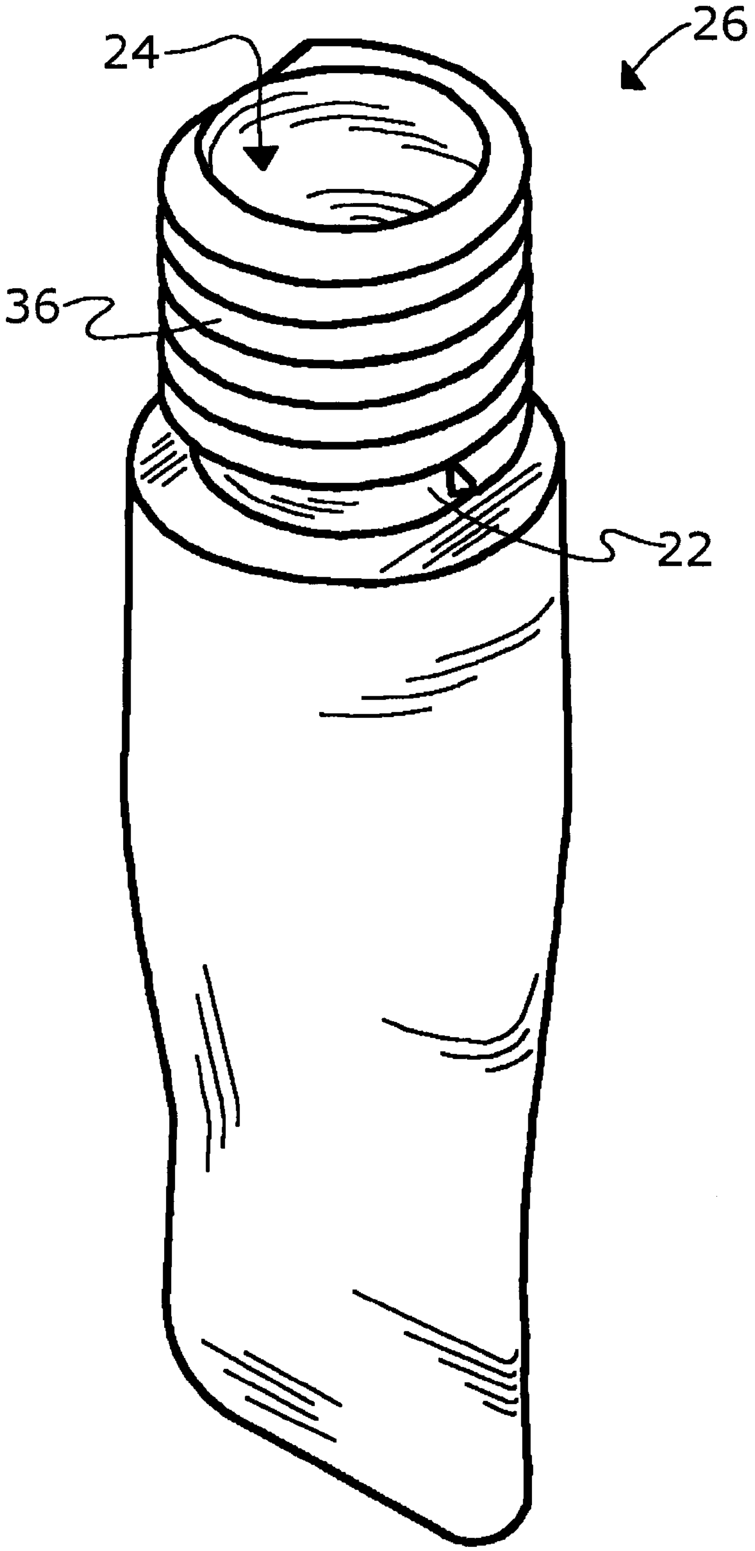
FIG. 11 is an isometric view of the front, top, and right sides of a first chamber of a medication dispenser according to the first embodiment of a dispensing system with the breakable membrane removed.
Figure 12:
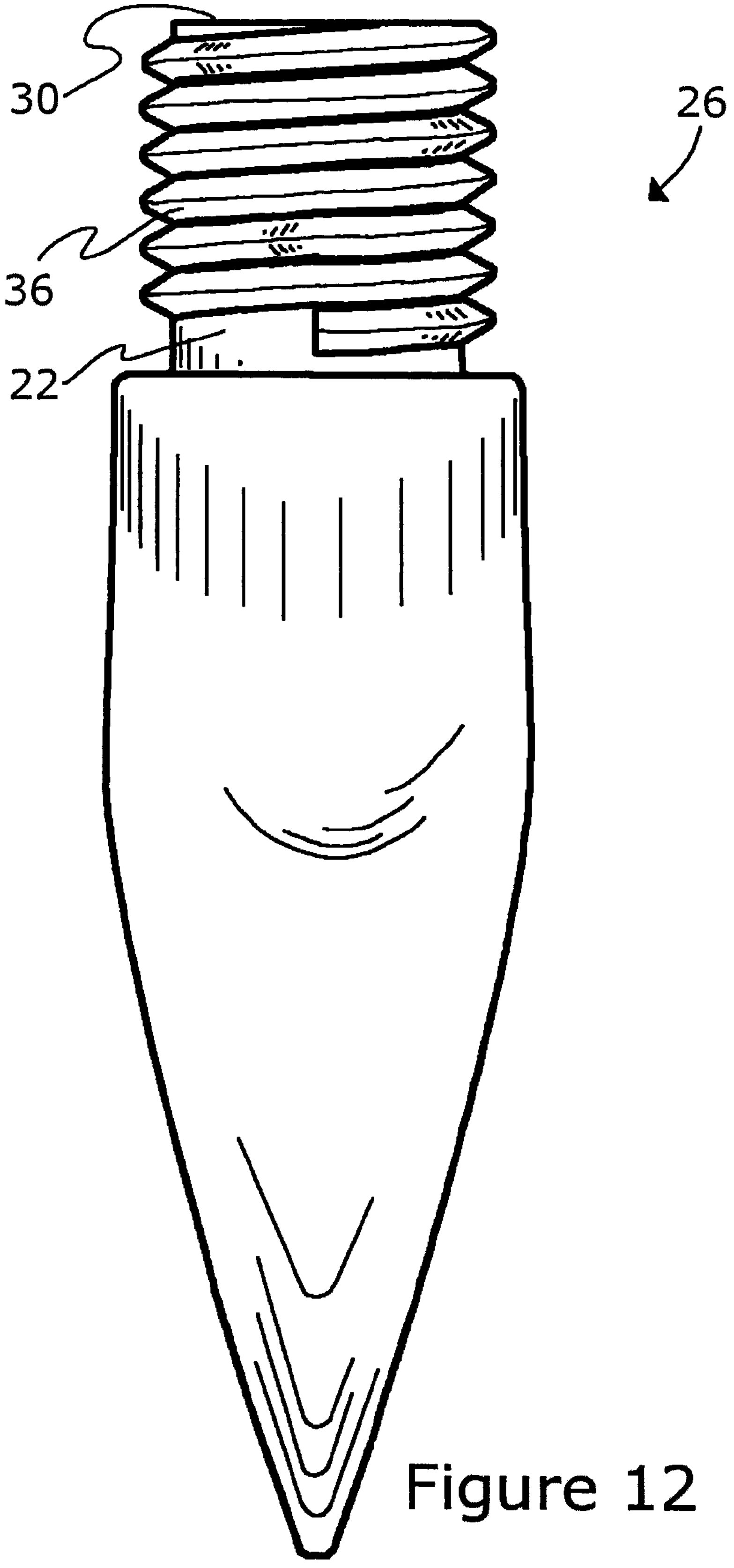
FIG. 12 is an elevation view of the right side of a first chamber of a medication dispenser according to the first embodiment of a dispensing system.

As shown in the figures, the dispensing system includes a dispenser 12 and a storage container 80. According to a first embodiment, the dispenser 12 includes a first chamber 26 that has an open top end 24. First screw threads 36 line an upper area of the first chamber 26's external surface 22. The first chamber 26 is at least partially compressible, preferably laterally compressible. At least before use, the first chamber 26 contains a first material, such as a fluid. According to the preferred embodiments, the first material is a fluid, specifically a reconstituting fluid 32. In some embodiments, such as the embodiment depicted in FIG. 18, the reconstituting fluid 32 is a liquid such as water. In other embodiments, the reconstituting fluid 32 is a gas such as air. Further, at least before use, the open top end 24 (shown in FIG. 11) is covered by a breakable membrane 30 (shown in FIG. 10). The breakable membrane 30 closes off the open top end 24 so that the reconstituting fluid 32 is contained within the first chamber 26.

Figure 13:
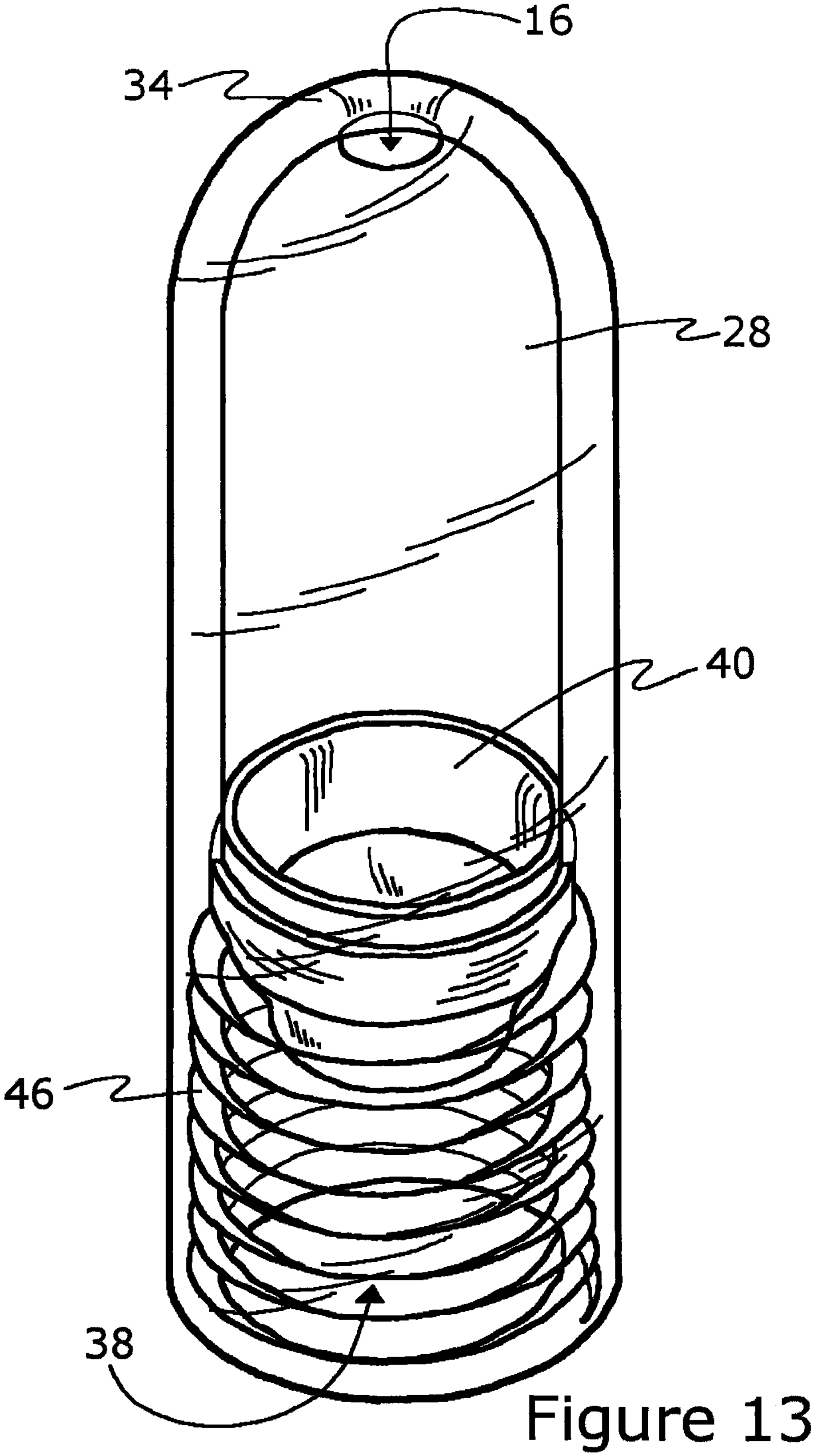
FIG. 13 is an isometric view of the front, top, and right sides of a second chamber and breaker ring of a medication dispenser according to the first embodiment of a dispensing system with the breakable membrane removed.
Figure 15:
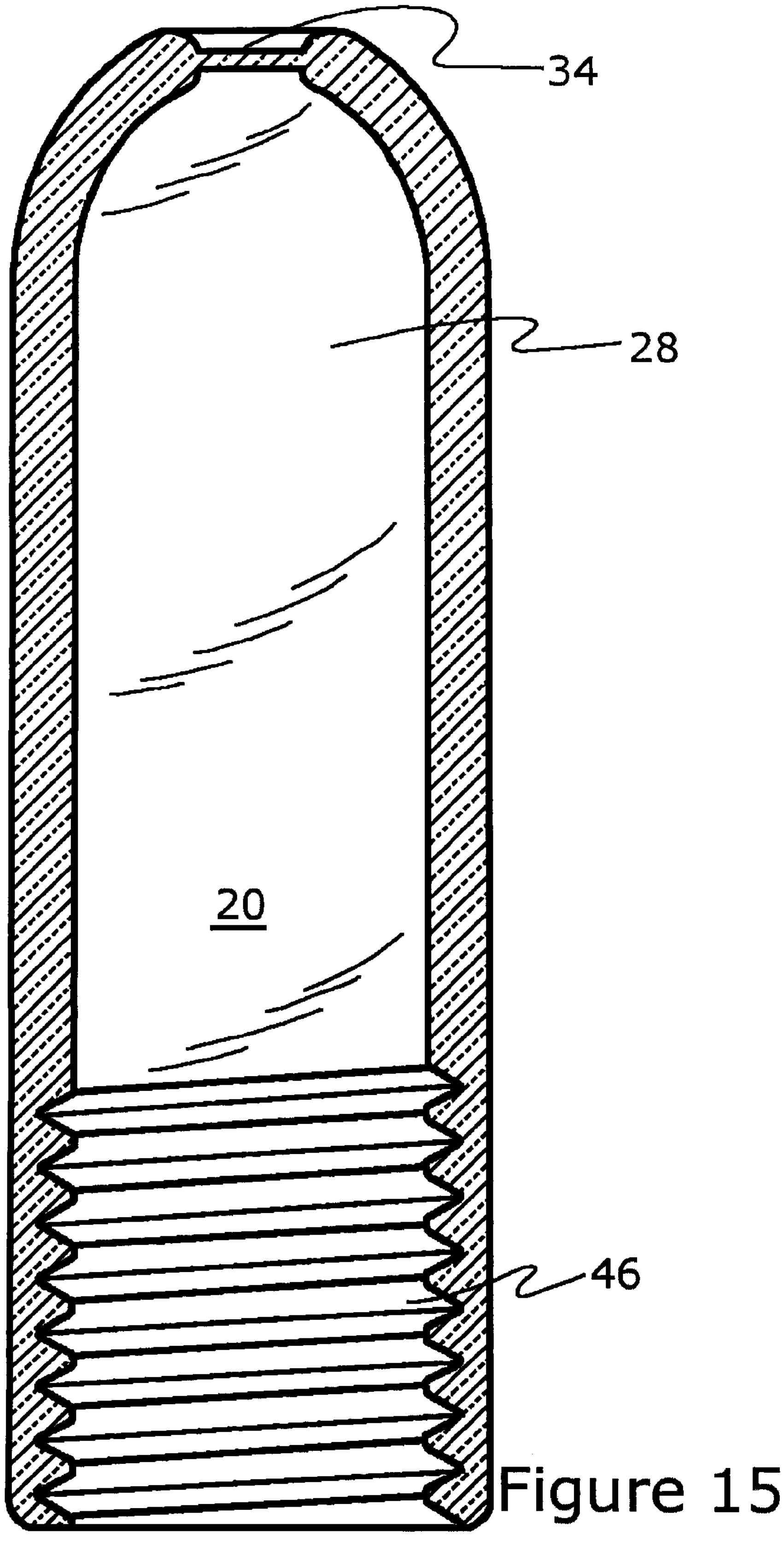
FIG. 15 is a cross-sectional, elevation view taken along line A-A from the left side, of a second chamber of a medication dispenser according to the first embodiment of a dispensing system.
Figure 18:
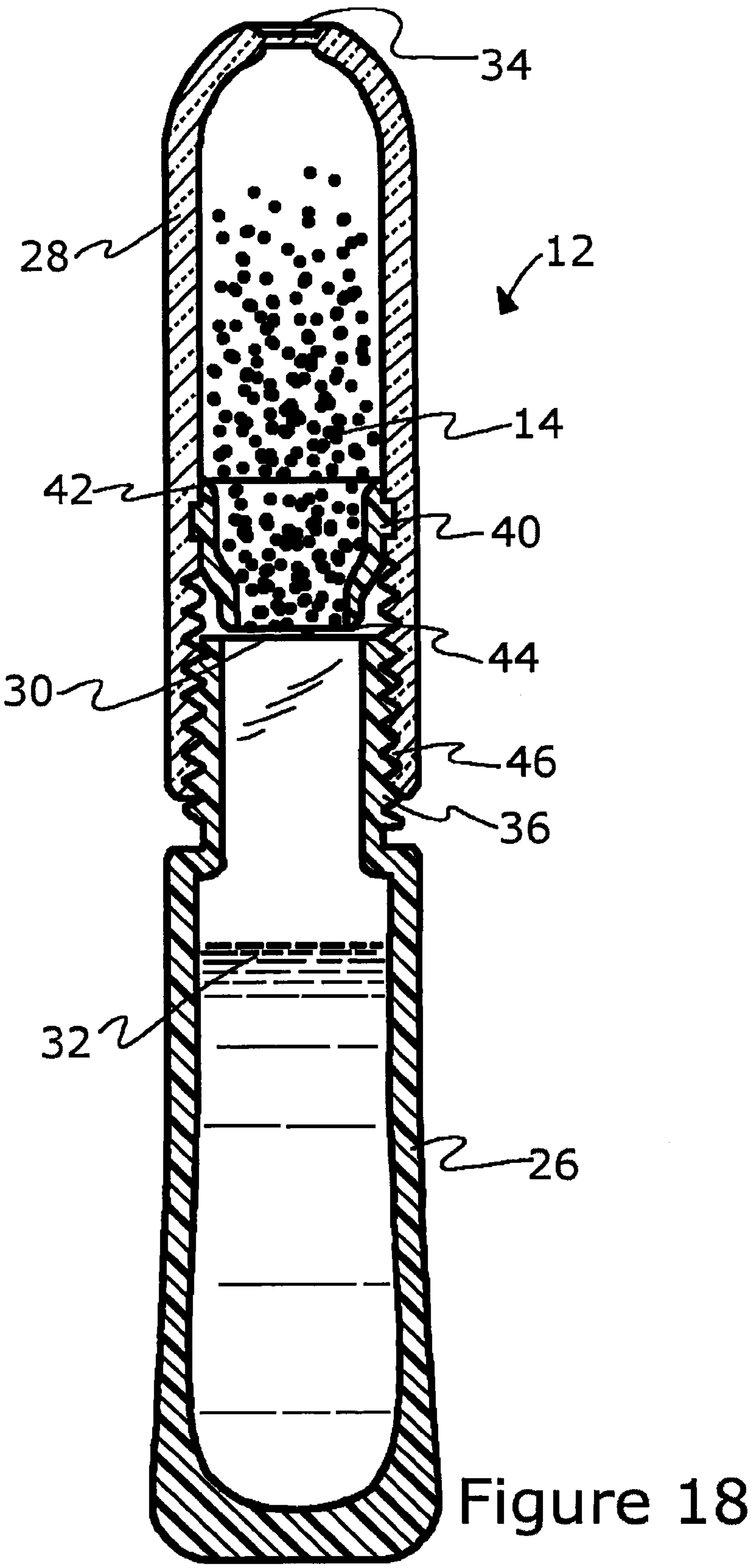
FIG. 18 is a cross-sectional, elevation view, taken along line A-A from the front side, of a medication dispenser containing medication and reconstituting fluid according to the first embodiment of a dispensing system where the dispenser is in an extended position.
Figure 19:
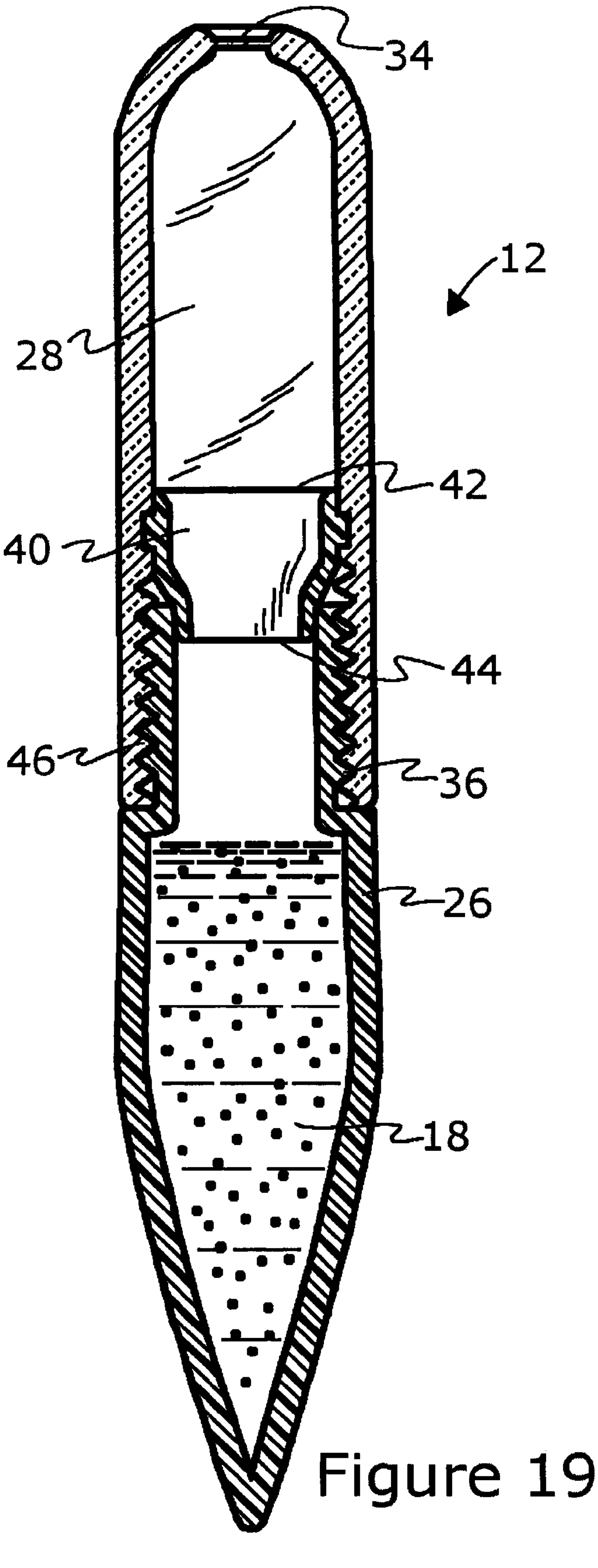
FIG. 19 is a cross-sectional, elevation view taken along line B-B from the right side, of a medication dispenser containing medication and reconstituting fluid according to the first embodiment of a dispensing system where the dispenser is in a compact position.

The dispenser 12 of the depicted embodiments further includes a second chamber 28 that has an open bottom end 38 (shown in FIG. 13). Second screw threads 46 line a lower area of the second chamber 28's internal surface 20. Preferably, the second screw threads 46 are recessed within the wall of the second chamber 28, as shown in FIG. 15. This minimizes the bulk of the second chamber 28 and thus the bulk of the dispenser 12 itself. Contained within the second chamber 28 is a second material, preferably the second material is a medication 14, preferably in a solid, powder form (as shown in FIG. 18). In other embodiments, the second material is a second fluid, such as a medication in liquid form.

The second chamber 28 further includes an openable tip 34, preferably at the upper-most portion of the second chamber 28. In the depicted embodiments, the openable tip 34 is a relatively thin layer plastic (shown in FIG. 14) that is puncturable to form an opening 16 (shown in FIGS. 13). In other embodiments, the openable tip 34 is an opening covered by a removable tab. In still other embodiments, the openable tip 34 is a relatively thin layer of plastic that can be removed by snipping off the openable tip 34 or by ripping off the openable tip 34. In further embodiments, the openable tip 34 is also fitted with an attachment configured to connect the dispenser 12 with an intravenous line.

Figure 14:
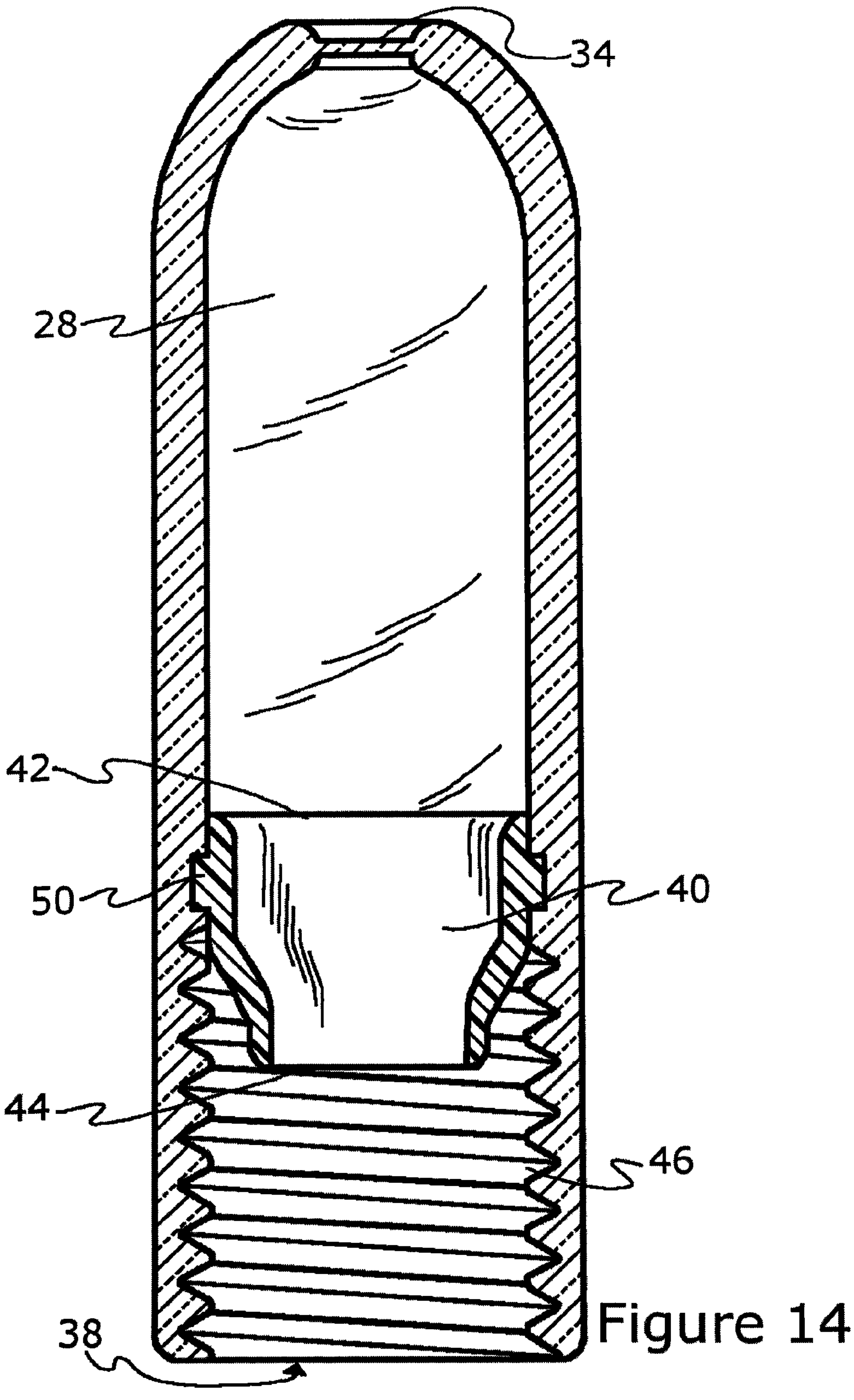
FIG. 14 is cross-sectional, elevation view taken along line A-A from the left side, of a second chamber and breaker ring of a medication dispenser according to the first embodiment of a dispensing system.

Also, according to the depicted embodiments, the dispenser 12 further includes a breaker ring 40 within the second chamber 28, situated above the second screw threads 46. Preferably, the breaker ring 40 is fixedly connected to the internal surface 20 of the second chamber 28 via a peripheral protrusion 50. Preferably, the peripheral protrusion 50 comprises a ring protruding from the side of the breaker ring 40 where the circumference of the peripheral protrusion 50 is greater than the circumference of the wide upper edge 42. The peripheral protrusion 50 protrudes into and is received within the wall of the second chamber 28, as shown in FIG. 14. In some embodiments, the breaker ring 40 tapers from a wide upper edge 42 to a narrow lower edge 44, the peripheral protrusion 50 being located therebetween. According to the depicted embodiments, the circumference of the wide upper edge 42 is greater than the circumference of the narrow lower edge 44, and the breaker ring 40 is open at both the wide upper edge 42 and narrow lower edge 44. The narrow lower edge 44 is configured to be received within the open top end 24 of the first chamber 26 when the breakable membrane 30 is broken or not in place. That is, preferably, the circumference of the exterior of the narrow lower edge 44 is less than the circumference of the interior of the open top end 24.

The second screw threads 46 of the second chamber 28 are configured to correspond with the first screw threads 36 of the first chamber 26 such that the second chamber 28 and first chamber 26 are configured to be selectively joinable to one another via interaction of the first screw threads 36 and second screw threads 46. Correspondingly, the first chamber 26 and second chamber 28 are configured to be selectively disconnected from one another via interaction of the first screw threads 36 and the second screw threads 46. For example, in some embodiments, the screw threads 36, 46 are configured such that a clockwise rotation of the first chamber 26 relative to the second chamber 28 will draw the two chambers 26, 28 into closer proximity with one another while a counterclockwise rotation of the first chamber 26 relative to the second chamber 28 will move the two chambers 26, 28 further away from one another, eventually disconnecting the chambers 26, 28 from one another. As shown in the figures, twisting the second chamber 28 relative to the first chamber 26 to join the two together effectively closes the second chamber 28 to prevent the material within, such as the medication 14 depicted in FIG. 18, from leaving the dispenser 12.

Figure 9:
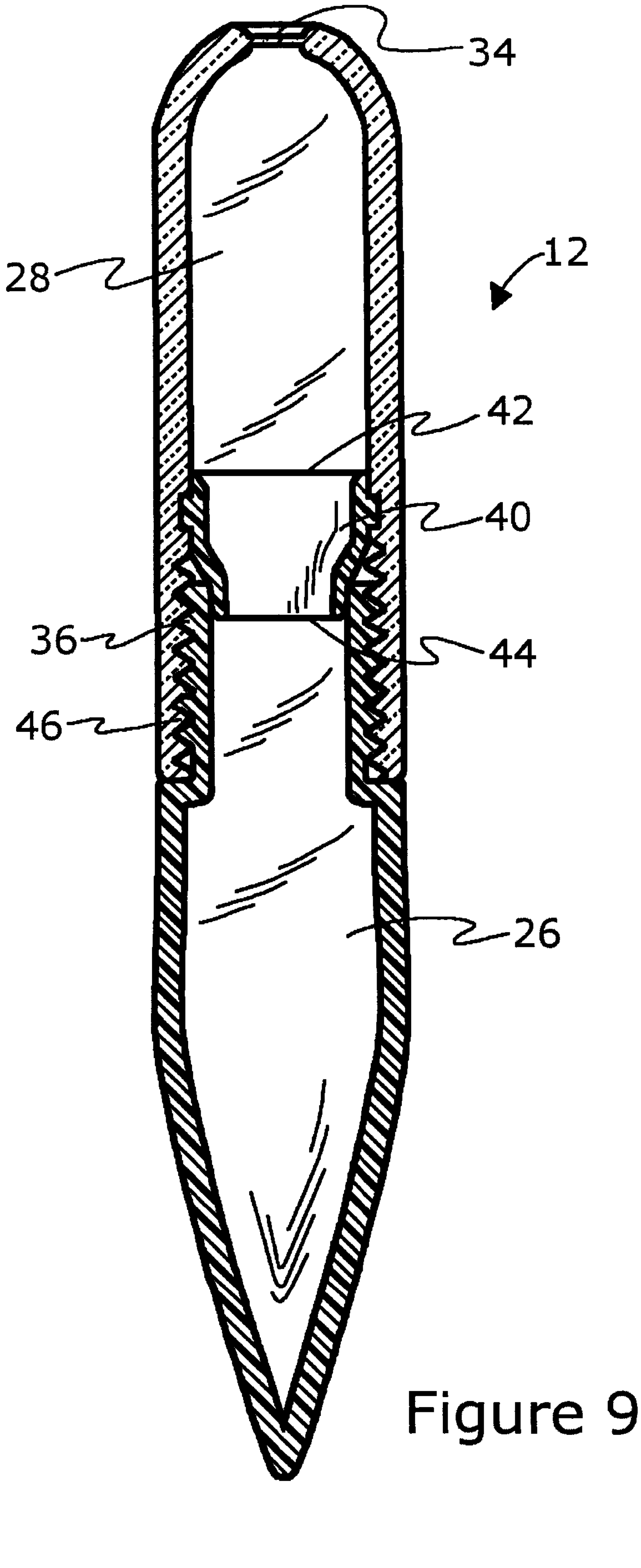
FIG. 9 is a cross-sectional, elevation view taken along line B-B from the right side, of a medication dispenser according to the first embodiment of a dispensing system where the dispenser is in a compact position.

Ideally, during transport and storage, at least before use, the first chamber 26 and second chamber 28 are joined and arranged in an extended position, shown in FIGS. 1 through 5 and 18, in which the narrow lower edge 44 of the breaker ring 40 is external to the second chamber 28 and is not in contact with the breakable membrane 30. The first chamber 26 and second chamber 28 are further twistable, relative to one another, via interaction of the second screw threads 46 and first screw threads 36, so that the second chamber 28 and first chamber 26 are brought into closer proximity to one another. Enough twisting eventually transitions the dispenser 12 to a compact position, shown in FIGS. 9 and 18. In the compact position, the narrow lower edge 44 of the breaker ring 40 is received within the open top end 24 of the first chamber 26. During twisting of the first chamber 26 and second chamber 28 relative to one another to transition the dispenser 12 from the extended position to the compact position, the narrow lower edge 44 of the breaker ring 40 is brought into forced contact with the breakable membrane 30 covering the open top end 24 of the first chamber 26. Additional twisting results in the narrow lower edge 44 breaking the breakable membrane 30. Once the breakable membrane 30 is broken, the first chamber 26 and second chamber 28 form a joined chamber within the dispenser 12. Accordingly, the medication 14 that was originally contained within the second chamber 28 and the reconstituting fluid 32 that was originally contained with the first chamber 26 can mix and form a medication mixture 18. Ideally, the medication 14 may be shaken or otherwise agitated to encourage mixing of the medication 14 and reconstituting fluid 32 between the two chambers 26, 28. It is further preferable that the first screw threads 36 of the first chamber 26 and the second screw threads 46 of the second chamber 28 are configured to form a fluid-tight seal so that, once the breakable membrane 30 is broken, none of the reconstituting fluid 32 or medication mixture 18 will unintentionally leave the dispenser 12.

Figure 16:
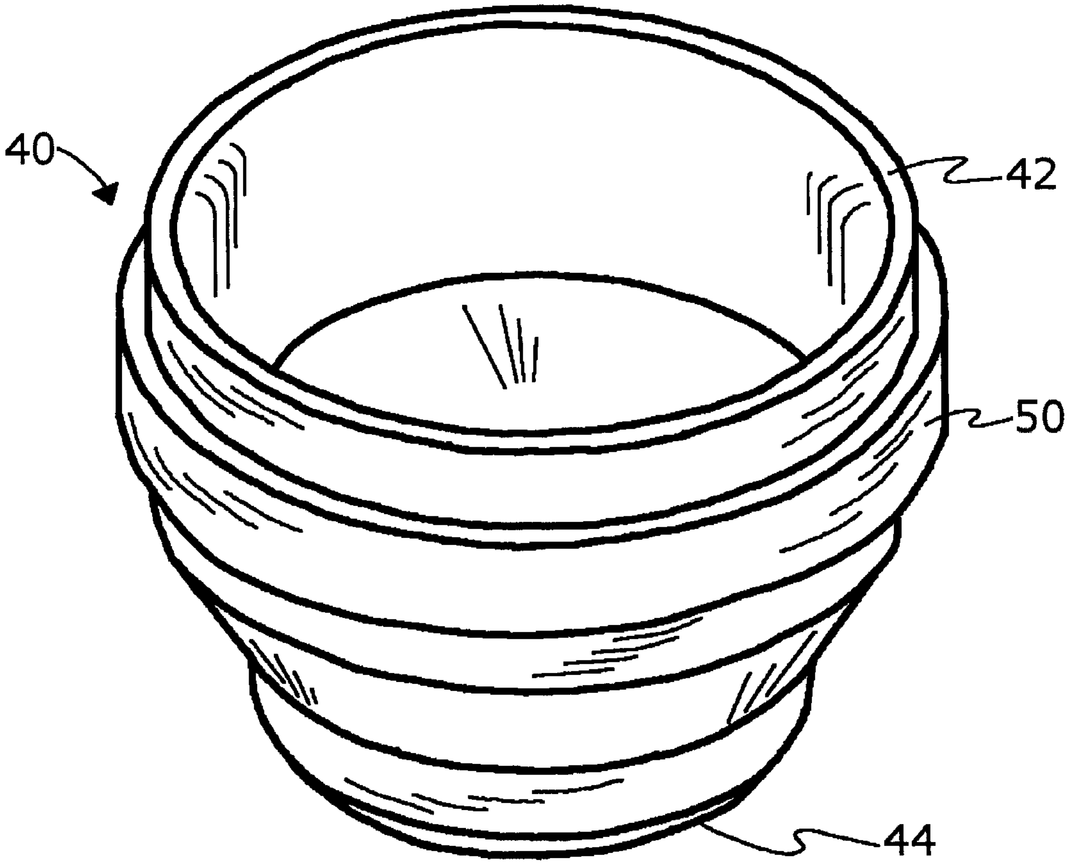
FIG. 16 is an isometric view of the front and top sides of a breaker ring of a medication dispenser according to the first embodiment of a dispensing system.
Figure 17:
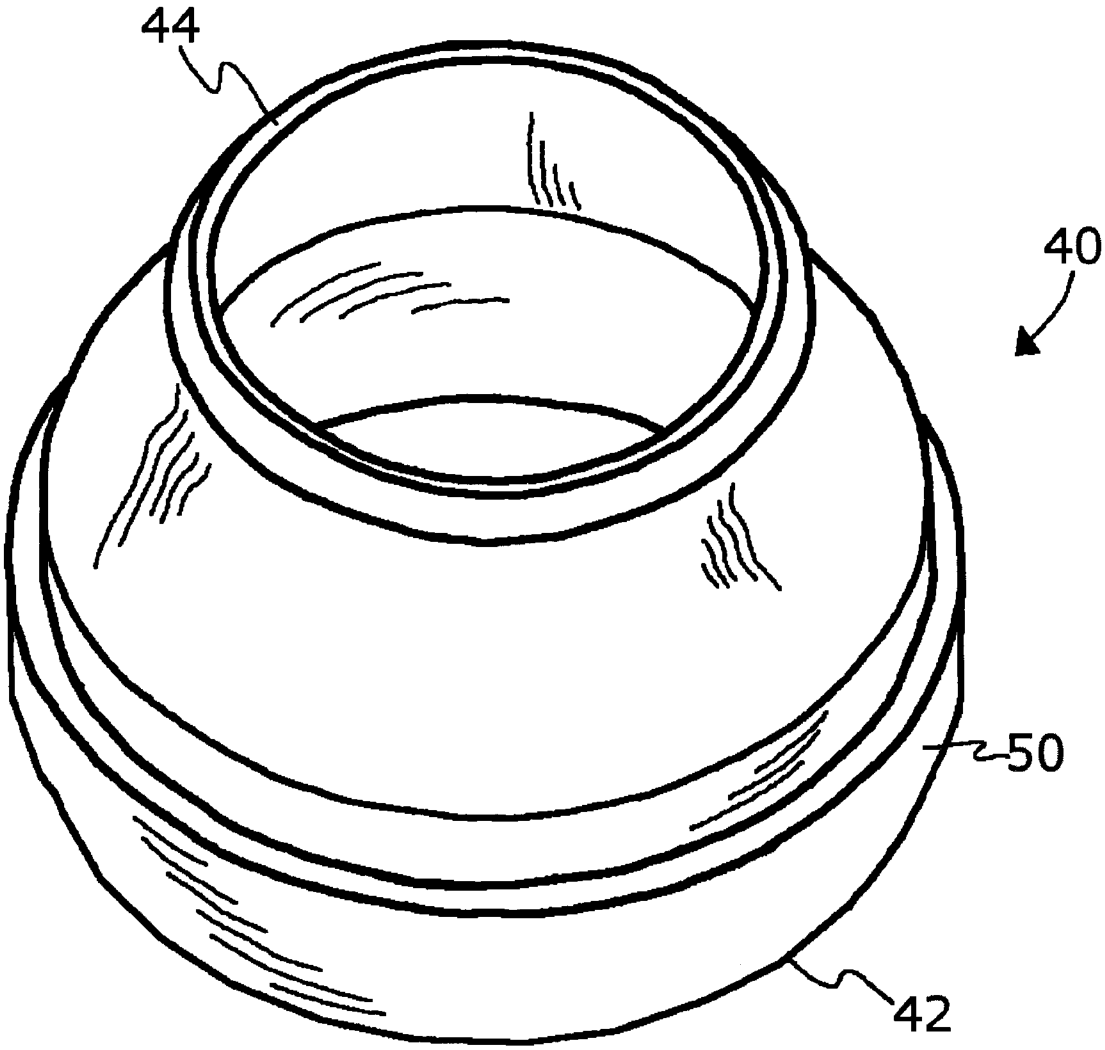
FIG. 17 is an isometric view of the back and bottom sides of a breaker ring of a medication dispenser according to the first embodiment of a dispensing system.

The breaker ring 40 of the first depicted embodiment, shown in FIGS. 16 and 17, includes a narrow lower edge 44 that is smooth and even along its edge. According to the first depicted embodiment, the narrow lower edge 44 defines a lower plane that is essentially parallel to an upper plane defined by the wide upper edge 42. Such lower plane and upper plane are also essentially parallel to the middle plane defined by the peripheral protrusion 50.

Figure 20:
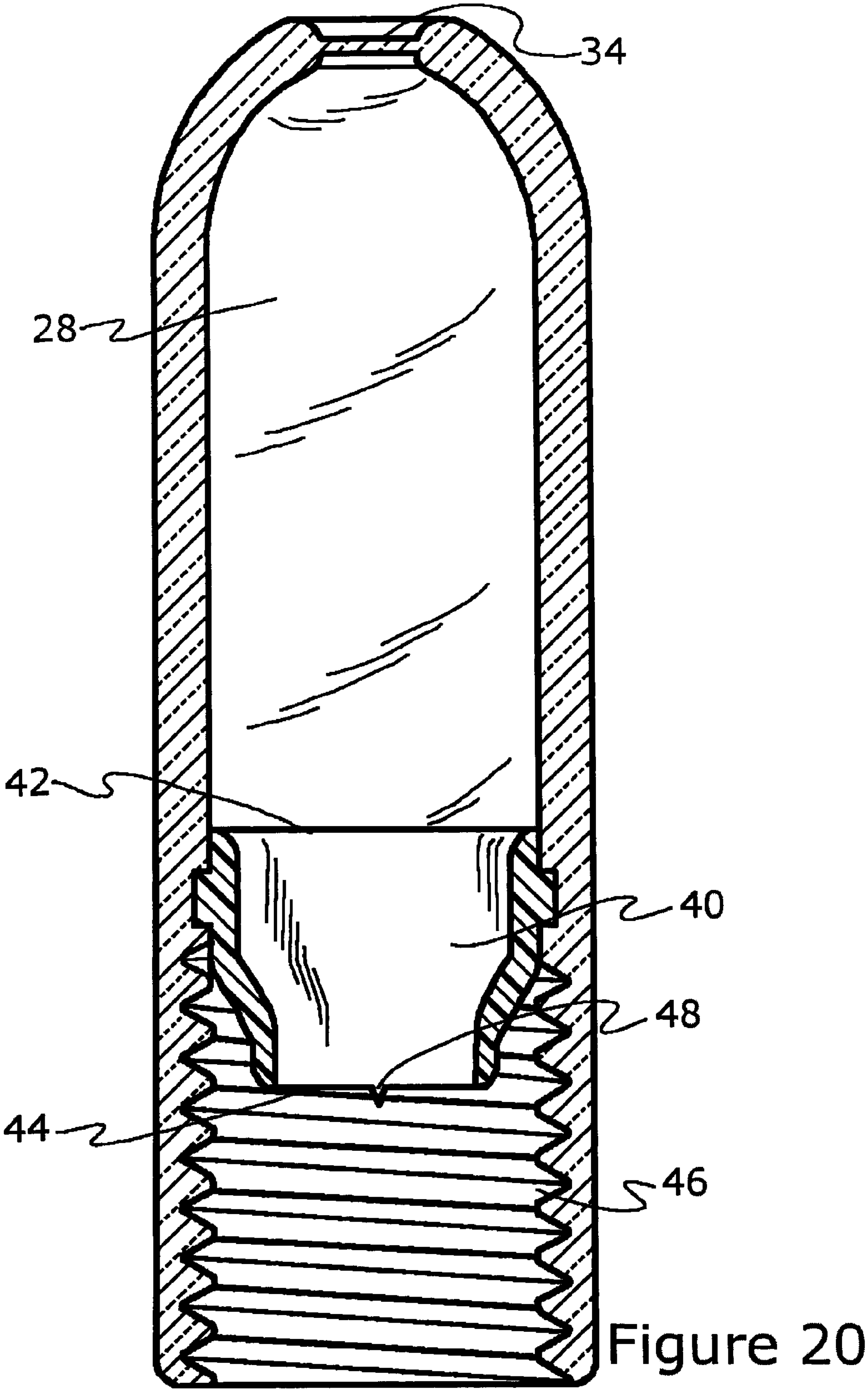
FIG. 20 is cross-sectional, elevation view taken along line A-A from the left side, of a second chamber and breaker ring of a medication dispenser according to the second embodiment of a dispensing system.
Figure 21:
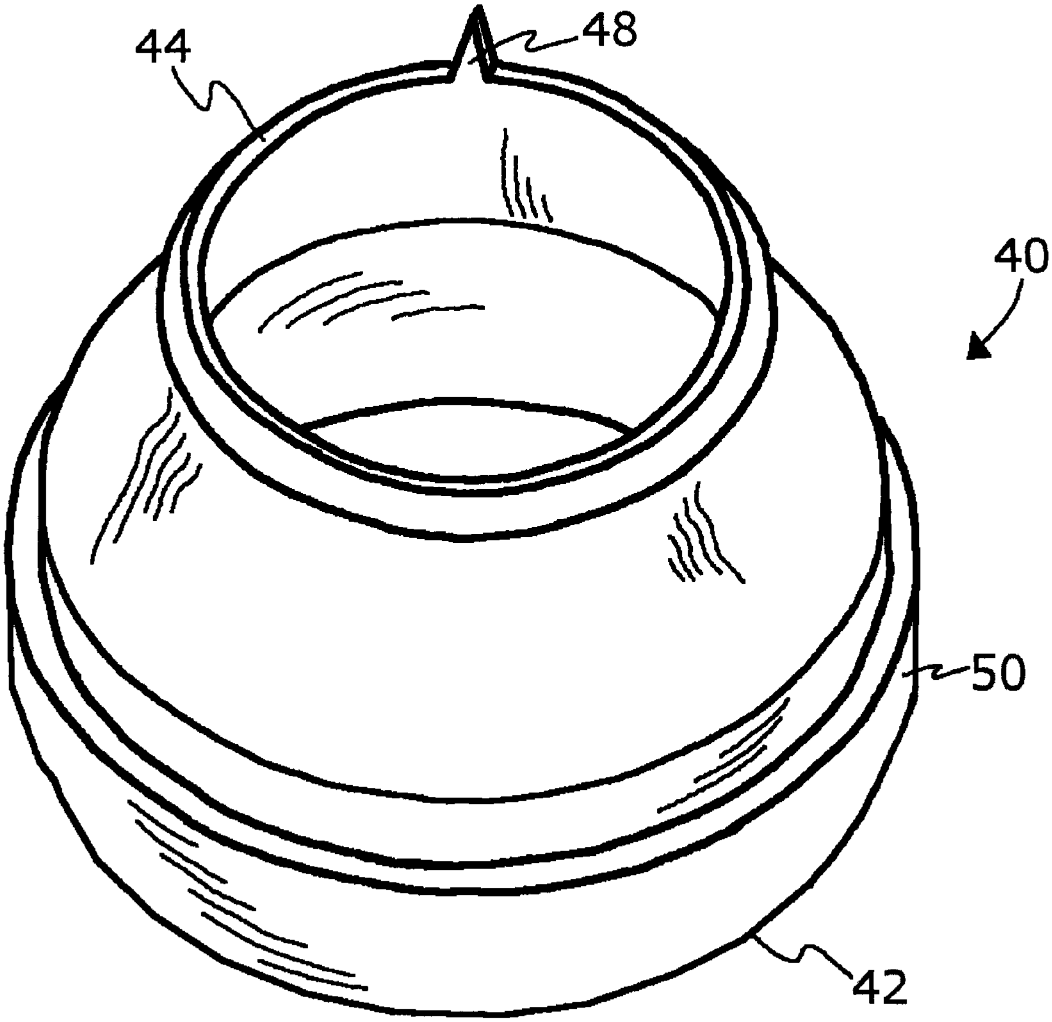
FIG. 21 is an isometric view of the back and bottom sides of a breaker ring of a medication dispenser according to the second embodiment of a dispensing system.

The breaker ring 40 of the second depicted embodiment, shown in FIGS. 20 and 21, includes a narrow lower edge 44 that has a protruding member 48. The protruding member 48 is configured to break the breakable membrane 30 upon forced contact with the breakable membrane 30. Preferably, the protruding member 48 is a sharp point. As such, forced contact of the tip of the sharp point with the breakable membrane 30 will result in first a puncturing of the breakable membrane 30 followed by a general breakage of the breakable membrane 30 as the breaker ring 40 is brought into further forced contact with the breakable membrane 30 as the first chamber 26 and second chamber 28 are twisted relative to one another. In other embodiments, the breaker ring 40 includes a number of protruding member 48*s* along the narrow lower edge 44.

Figure 22:
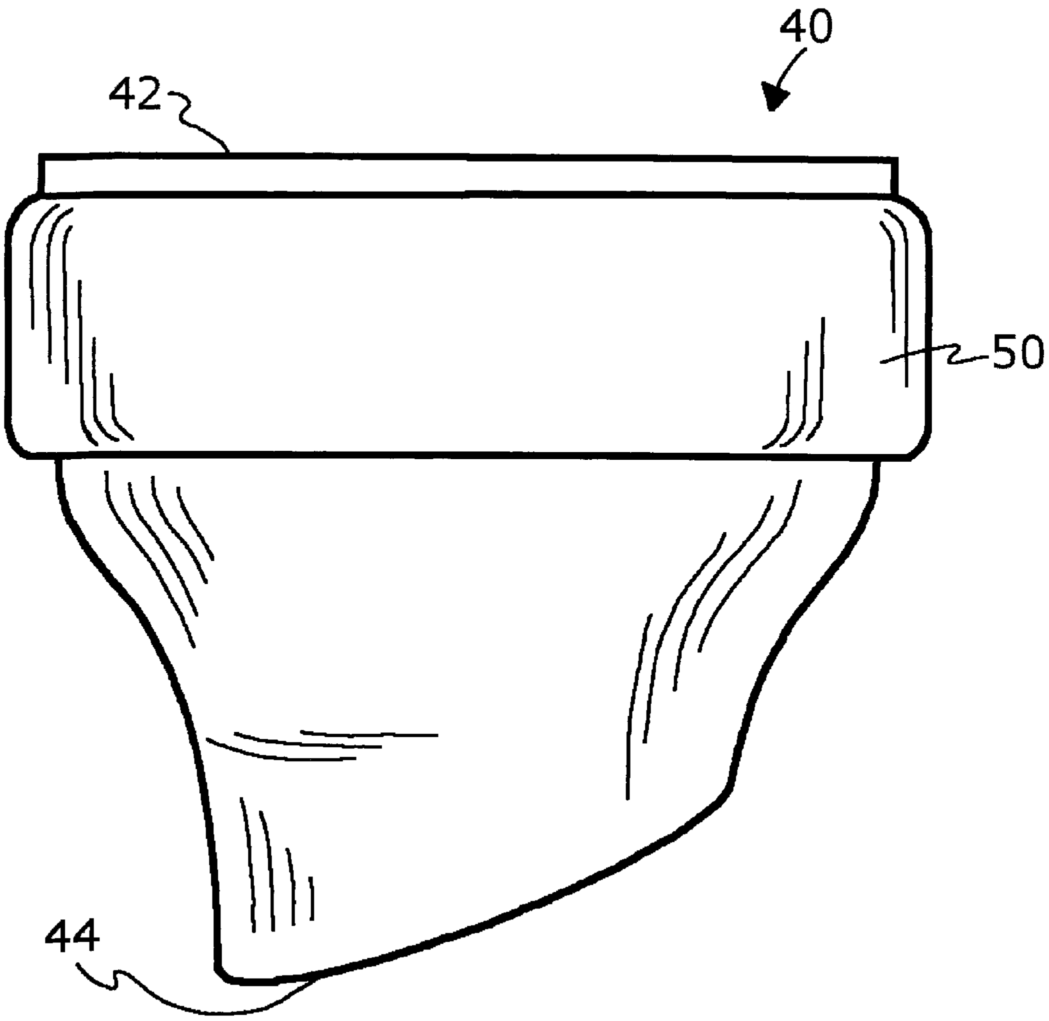
FIG. 22 is an elevation view of the front side of a breaker ring of a medication dispenser according to a third embodiment of a dispensing system.

The breaker ring 40 of the third depicted embodiment, shown in FIG. 22, includes a narrow lower edge 44 that is smooth and even along its edge. Further the narrow lower edge 44 defines a lower plane that is not parallel to an upper plane defined by the wide upper edge 42. Rather, the narrow lower edge 44 of the breaker ring 40, according to the third depicted embodiment, slants such that one area of the narrow lower edge 44 will come into contact with the breakable membrane 30 first, before the other areas of the narrow lower edge 44 as the dispenser 12 is transitioned between the extended position and the compact position. As such, the forced interaction of the narrow lower edge 44 and the breakable membrane 30 will, at least at first, be concentrated on the lowest area of the narrow lower edge 44, encouraging breakage of the breakable membrane 30 in that area of contact.

To dispense the medication mixture 18 to a patient, once the breakable membrane 30 is broken and the dispenser 12 twisted so that it is in the compact position, the openable tip 34 can be opened so as to form an opening 16. Thereafter, the first chamber 26 may be compressed so as to force the medication mixture 18 out of the first chamber 26, through the breaker ring 40, and out of the second chamber 28 via the opening 16. In some situations, the first chamber 26 is compressed due to physical squeezing of the first chamber 26. In other situations, the first chamber 26 is compressed due to the application of suction within the dispenser 12.

The dispenser 12 is further figured such that the material within the first chamber 26 can be dispensed without opening the openable 34. That is, the first chamber 26 and second chamber 28 can be selectively disconnected from one another via twisting in the opposite direction that one would twist to transition the dispenser 12 from the extended position to the compact position. This twisting will eventually separate the two chambers 26, 28 from each other. Thereafter, the material within the second chamber 28, such as the medication 14, can be emptied via the open bottom end 38. Alternatively or additionally, the breakable membrane 30 can be broken with means other than the breaker ring 40, such as by application of pressure with a finger or fingernail against the breakable membrane 30 or with the use of a separate puncturing device, so as to make accessible the open top end 24. Thereafter, the material within the first chamber 26 can be emptied via the open top end 24. Accordingly, separation of the two chambers 26, 28 from one another provides an option for dispensing of the medication to a patient without mixing the materials 14, 32. Further, the separation of the two chambers 26, 28 allows a user to refill or replace material within one or the other chamber 26, 28 before or without mixing the materials.

In some embodiments, the dispenser 12 is configured to be disposable, such that after dispensing the medication mixture 18, the entire dispenser 12 can be discarded or recycled. In other embodiments, the dispenser 12 is configured to be reusable, such that the first chamber 26 and second chamber 28 are twisted relative to one another in such a manner as to transition the dispenser 12 from the compact position to the extended position and then to disconnect the second chamber 28 from the first chamber 26. The first chamber 26 is then refilled with reconstituting fluid 32 and a new breakable membrane 30 put in place to cover the open top end 24. The opening 16 in the openable tip 34 is covered with a selectively removable tab and additional medication 14 filled into the second chamber 28. Thereafter, the refilled first chamber 26 and second chamber 28 are again rejoined into the extended position. This reuse may be repeated as desired.

According to the depicted embodiments, the medication 14 within the second chamber 28 is a solid powder. In other embodiments, the medication 14 is a medication in fluid form. In still other embodiments, the material within the second chamber 28 is a non-medicinal material. Further, according to the depicted embodiments, the second chamber 28 is made up of a translucent plastic that is noncompressible. Also according to the depicted embodiments, the first chamber 26 tapers in width along the lower part of the first chamber 26 such that the open top end 24 is broader than the bottom edge 52. In this way, the tapering section forms a handle. As it is preferred that the first chamber 26 be compressible, according to the depicted embodiments, the first chamber 26 is preferably compressible laterally, such that the individual dispensing the medication would squeeze along the tapering area.

Figure 23:
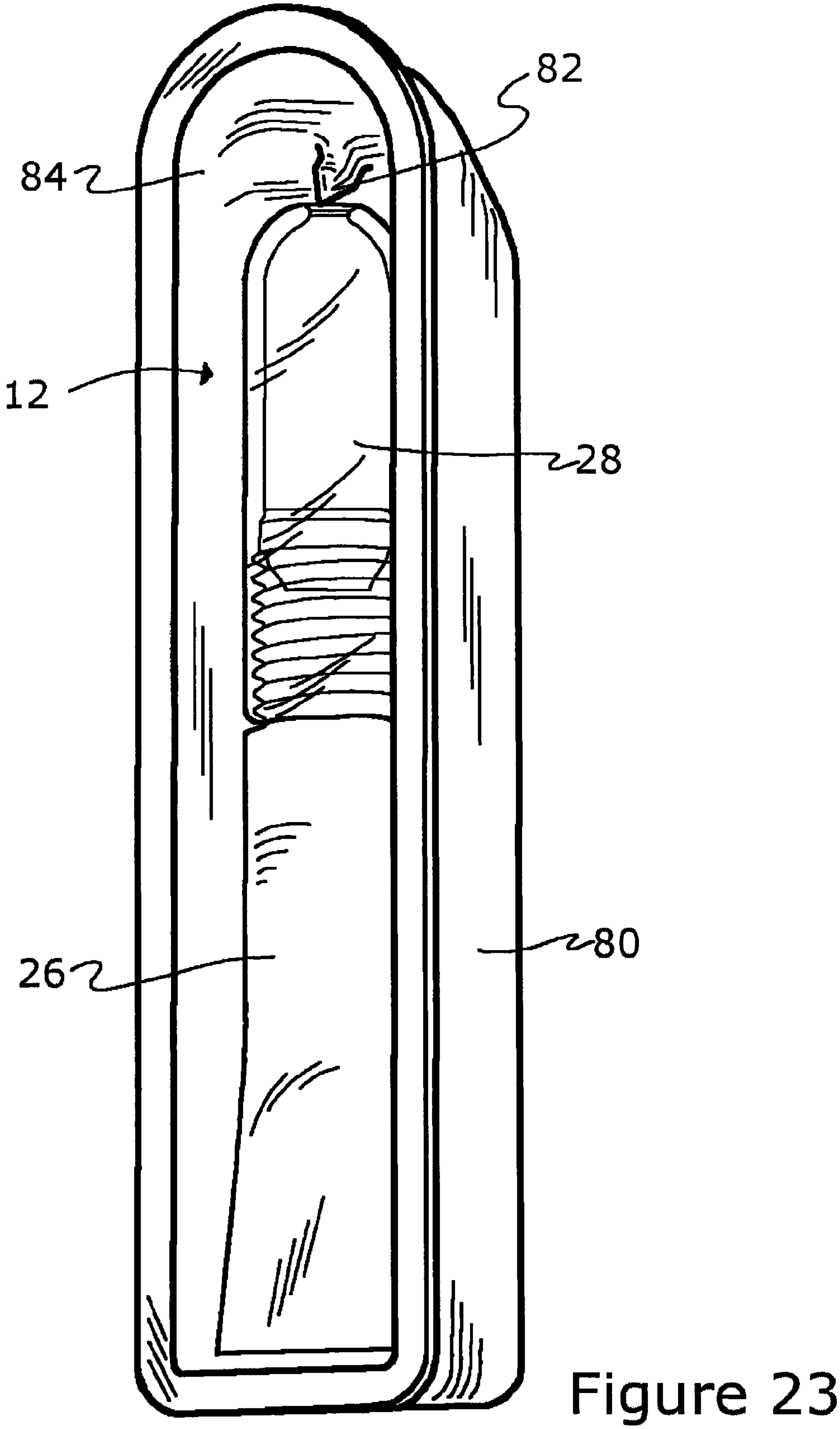
FIG. 23 is an isometric view of the front and right sides of a medication dispenser within a storage container according to the first embodiment of a dispensing system.
Figure 24:
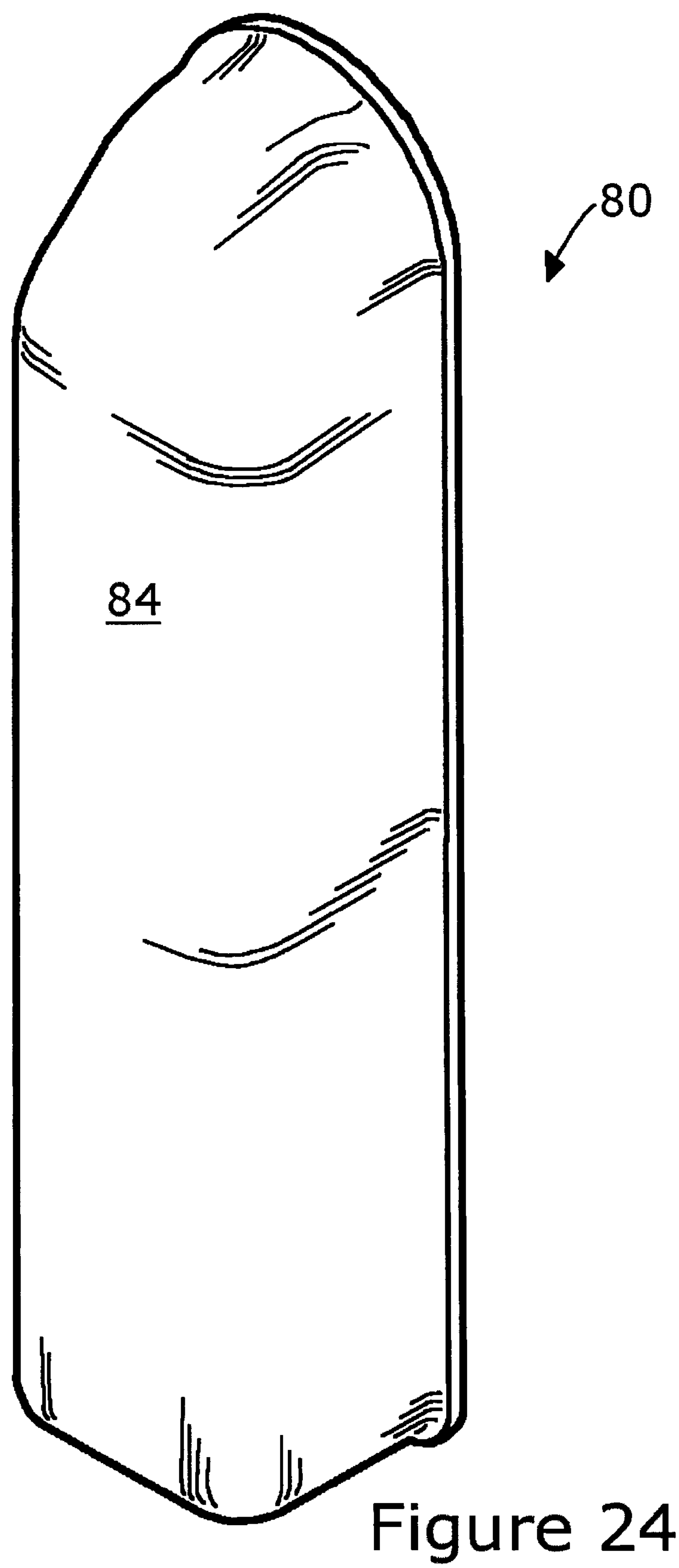
FIG. 24 is an isometric view of the back, top, and left sides of a medication dispenser within a storage container according to the first embodiment of a dispensing system.
Figure 25:
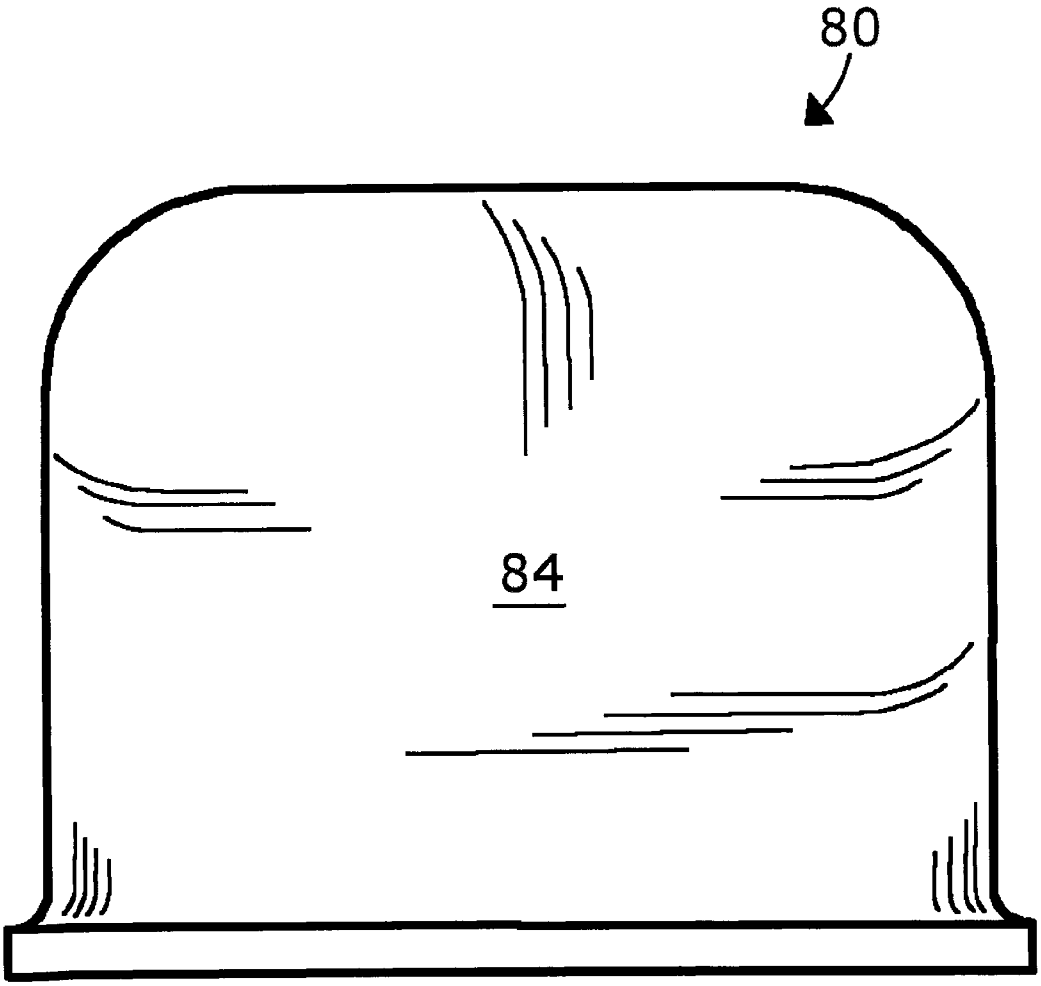
FIG. 25 is an elevation view of the bottom of a medication dispenser within a storage container according to the first embodiment of a dispensing system.

According to some embodiments, the openable tip 34 of the dispenser 12 is puncturable. As such, the dispenser 12 is configured to be utilized as the puncturable, compressible ampule of the oral liquid medication dispensing system for dispensing measured dosages of selected oral medication described in U.S. Pat. No. 7,452,350, the disclosure of which is incorporated herein by reference in its entirety. Further, the dispenser 12 is configured to be utilized with the storage container 80 of the depicted dispensing system, as shown in FIGS. 23 through 25. The depicted storage container 80 of the dispensing system includes a container wall 84 that is configured to receive within the dispenser 12. The storage container 80 includes a puncturing device 82 (FIG. 23). Preferably, the puncturing device 82 is formed within a bottom portion of the container wall 84 of the storage device 80. In other embodiments, the puncturing device 82 is fixedly attached to the container wall 84. The puncturing device 82 protrudes from the container wall 84, and the puncturing device 82 is configured to enable puncturing of a puncturable openable tip 34 of the first chamber 26 of the dispenser 12. More particularly, the puncturing device 82 is configured such that manipulation of the dispenser 12 so as to position the openable tip 34 to be in forced contact with the puncturing device 82 will result in puncturing of the openable tip 34 with the opening 16 being created thereby. Preferably, the puncturing device 82 is calibrated to create an opening 16 of a pre-determined size. Also, preferably, the puncturing device 82 is recessed within the storage container 80, as shown in FIG. 23, so as to avoid unintended interaction with external items and to lessen the risk of unintended interaction with a user's fingers. The container wall 84 further defines an upper ridge forming the upper border of the storage container 80. In some embodiments, the storage container 80 is covered with a removable covering along the upper ridge, thereby providing additional protection to the dispenser 12 within the storage container 80 during transport or otherwise before use thereof.

The exemplary embodiments shown in the figures and described above illustrate, but do not limit, the dispensing system. It should be understood that there is no intention to limit the dispensing system to the specific form disclosed; rather, the dispensing system is to cover all modifications, alternative constructions, and equivalents falling within the spirit and scope of the dispenser as defined in the claims. For example, while the dispensing system is not limited to use with orally-administered medication, it is expected that various embodiments of the dispensing system will be particularly useful in such applications. Hence, the foregoing description should not be construed to limit the scope of the invention, which is defined in the following claims.

Accordingly, while there is shown and described the present preferred embodiments of the dispensing system, it is to be distinctly understood that this dispensing system is not limited thereto but may be variously embodied to practice within the scope of the following claims. From the foregoing description, it will be apparent that various changes may be made without departing from the spirit and scope of the invention, as defined by the following claims.

What is claimed is:

1. A medication dispenser comprising:
- a first chamber, said first chamber having an open top end, an external surface, and first screw threads lining an upper area of said external surface; said first chamber being at least partially compressible;
- a reconstituting fluid contained within said first chamber;
- a breakable membrane covering said open top end of said first chamber;
- a second chamber, said second chamber having an open bottom end, an internal surface, an openable tip, and second screw threads lining a lower area of said internal surface, said second chamber being selectively joinable to said first chamber via interaction of said first screw threads and said second screw threads;
- a pre-selected quantity of medication contained within said second chamber; and
- a breaker ring within said second chamber, situated above said second screw threads, said breaker ring having a lower edge configured to be received within said open top end of said first chamber;
- said first chamber being twistable relative to said second chamber via said first screw threads and said second screw threads to transition said medication dispenser from an extended position in which said lower edge is external to said second chamber and is not in contact with said breakable membrane to a compact position in which said lower edge is received within said open top end of said first chamber;
- said breaker ring being configured to break open said breakable membrane when said first chamber is twisted to transition said medication dispenser from said extended position to said compact position;
- said openable tip being configured to be selectively openable to form an opening;
- whereby twisting of said first chamber relative to said second chamber to transition said medication dispenser from said extended position to said compact position causes said breaker ring to break open said breakable membrane such that said medication within said second chamber and said reconstituting fluid within said first chamber mix to form a medication mixture; and
- whereby, following opening of said openable tip, compression of said first chamber while said medication dispenser is in said compact position forces said medication mixture out of said first chamber, through said breaker ring, and out of said second chamber via said opening.

2. The medication dispenser of claim 1, wherein said medication contained within said second chamber is a powder.

3. The medication dispenser of claim 1, wherein said second chamber comprises a translucent plastic.

4. The medication dispenser of claim 1, wherein said openable tip is puncturable.

5. The medication dispenser of claim 1, wherein said second chamber comprises a noncompressible plastic.

6. The medication dispenser of claim 1, wherein said first chamber tapers in width from said open top end to a bottom edge.

7. The medication dispenser of claim 1, wherein said breaker ring further has an upper edge, said upper edge defining an upper plane, said lower edge defining a lower plane, said lower plane being aligned so as to not be parallel to said upper plane.

8. A medication dispensing system comprising:
- a twistable medication dispenser comprising:
  - a first chamber, said first chamber having an open top end, an external surface, and first screw threads lining an upper area of said external surface; said first chamber being at least partially compressible;
  - a reconstituting liquid contained within said first chamber;
  - a breakable membrane closing said open top end of said first chamber;
  - a second chamber, said second chamber having an open bottom end, an internal surface, an openable tip, and second screw threads lining a lower area of said internal surface, said second chamber being selectively joinable to said first chamber via interaction of said first screw threads and said second screw threads;
  - a pre-selected quantity of powder medication contained within said second chamber; and
  - a breaker ring within said second chamber, situated above said second screw threads, said breaker ring being fixedly attached to said internal surface along a peripheral protrusion, said breaker ring tapering from a wide upper edge to a narrow lower edge, said narrow lower edge being configured to be received within said open top end of said first chamber, said breaker ring having a protruding member extending away from its narrow lower edge, said protruding member being configured to break said breakable membrane upon forced contact with said breakable membrane;
  - said first chamber being twistable relative to said second chamber via said first screw threads and said second screw threads to transition said twistable medication dispenser from an extended position in which said protruding member is external to said second chamber and is not in contact with said breakable membrane to a compact position in which said narrow lower edge is received within said open top end of said first chamber;
  - said protruding member being configured to break open said breakable membrane when said first chamber is twisted to transition said twistable medication dispenser from said extended position to said compact position;
  - said openable tip being configured to be selectively openable to form an opening;
- a storage container comprising:
  - a container wall configured to receive said twistable medication dispenser therein;
  - a puncturing device protruding from said container wall, said puncturing device configured to create said opening in said openable tip whereby twisting of said first chamber relative to said second chamber to transition said twistable medication dispenser from said extended position to said compact position causes said protruding member to break open said breakable membrane such that said medication within said second chamber and said reconstituting liquid within said first chamber mix to form a medication mixture; and whereby, following creation of said opening in said openable tip by said puncturing device, compression of said first chamber while said twistable medication dispenser is in said compact position forces said medication mixture out of said first chamber, through said breaker ring, and out of said second chamber via said opening.

9. The medication dispensing system of claim 8, wherein said medication contained within said second chamber is a powder.

10. The medication dispensing system of claim 8, wherein said second chamber comprises a translucent plastic.

11. The medication dispensing system of claim 8, wherein said openable tip is puncturable.

12. The medication dispensing system of claim 8, wherein said second chamber comprises a noncompressible plastic.

13. The medication dispensing system of claim 8, wherein said first chamber tapers in width from said open top end to a bottom edge.

14. The medication dispensing system of claim 8, wherein said protruding member comprises a sharp point.

15. The medication dispensing system of claim 8, wherein said puncturing device is calibrated to create said opening of a pre-determined size.

16. A twistable dispenser comprising:

a first chamber, said first chamber having an open top end, an external surface, and first screw threads lining an upper area of said external surface; said first chamber being at least partially compressible;

a first fluid contained within said first chamber;

a breakable membrane covering said open top end of said first chamber;

a second chamber, said second chamber having an open bottom end, an internal surface, an openable tip, and second screw threads lining a lower area of said internal surface, said second chamber being selectively joinable to said first chamber via interaction of said first screw threads and said second screw threads;

a second fluid contained within said second chamber; and a breaker ringer within said second chamber, situated above said second screw threads, said breaker ring tapering from a wide upper edge to a narrow lower edge, said narrow lower edge being configured to be received within said open top end of said first chamber;

said first chamber being twistable relative to said second chamber via said first screw threads and said second screw threads to transition said dispenser from an extended position in which said narrow lower edge is external to said second chamber and is not in contact with said breakable membrane to a compact position in which said narrow lower edge is received within said open top end of said first chamber;

said breaker ring being configured to break open said breakable membrane when said first chamber is twisted to transition said dispenser from said extended position to said compact position;

said openable tip being configured to be selectively openable to form an opening;

whereby twisting of said first chamber relative to said second chamber to transition said dispenser from said extended position to said compact position causes said breaker ring to break open said breakable membrane such that said second fluid within said second chamber and said first fluid within said first chamber mix to form a fluid mixture; and whereby, following opening of said openable tip, compression of said first chamber while said dispenser is in said compact position forces said fluid mixture out of said first chamber, through said breaker ring, and out of said second chamber via said opening.

* * * * *